US011690877B2

(12) United States Patent
Shin et al.

(10) Patent No.: US 11,690,877 B2
(45) Date of Patent: Jul. 4, 2023

(54) UMBILICAL CORD-DERIVED ADHERENT STEM CELLS, PREPARATION METHOD THEREFOR, AND USE THEREOF

(71) Applicant: CHA BIOTECH CO., LTD., Gangnam-gu (KR)

(72) Inventors: Jeong Min Shin, Seongnam-si (KR); Ji Min Yu, Seongnam-si (KR); Jihye Kim, Suwon-si (KR); Ahreum Kang, Seongnam-si (KR); Hye Sun Kim, Seongnam-si (KR)

(73) Assignee: CHA BIOTECH CO., LTD., Gangnam-gu (KR)

( * ) Notice: Subject to any disclaimer, the term of this patent is extended or adjusted under 35 U.S.C. 154(b) by 254 days.

(21) Appl. No.: 15/752,057

(22) PCT Filed: Aug. 12, 2016

(86) PCT No.: PCT/KR2016/008887
§ 371 (c)(1),
(2) Date: Feb. 12, 2018

(87) PCT Pub. No.: WO2017/026838
PCT Pub. Date: Feb. 16, 2017

(65) Prior Publication Data
US 2018/0236007 A1      Aug. 23, 2018

(30) Foreign Application Priority Data

Aug. 12, 2015   (KR) .................. 10-2015-0113858
Aug. 12, 2016   (KR) .................. 10-2016-0102721

(51) Int. Cl.
| *A61K 35/00*  | (2006.01) |
| *A61K 35/50*  | (2015.01) |
| *A61K 35/51*  | (2015.01) |
| *A61P 25/00*  | (2006.01) |
| *A61P 37/00*  | (2006.01) |
| *A61P 9/00*   | (2006.01) |
| *C12N 5/0775* | (2010.01) |
| *C12N 5/0789* | (2010.01) |

(52) U.S. Cl.
CPC .............. *A61K 35/50* (2013.01); *A61K 35/51* (2013.01); *A61P 9/00* (2018.01); *A61P 25/00* (2018.01); *A61P 37/00* (2018.01); *C12N 5/0665* (2013.01); *C12N 5/0647* (2013.01); *C12Y 304/24003* (2013.01)

(58) Field of Classification Search
CPC ........................ A61K 35/51; C12N 5/0665
See application file for complete search history.

(56) References Cited

U.S. PATENT DOCUMENTS 9,803,176 B2       10/2017 Patel
2006/0223177 A1    10/2006 Harris et al.
2010/0143312 A1     6/2010 Hariri et al.
2012/0315251 A1    12/2012 Harris et al.
2014/0234968 A1     8/2014 Chung et al.
2014/0295554 A1    10/2014 Kim et al.
2014/0341867 A1    11/2014 Zeitlin et al.
2014/0348802 A1    11/2014 Shoemaker et al.
2015/0064273 A1     3/2015 Peled et al.
2015/0104470 A1     4/2015 Riordan
2015/0125950 A1 *   5/2015 Lim ................ C12N 5/0668
                                                     435/325

FOREIGN PATENT DOCUMENTS

| EP | 1 831 356           | 9/2007  |           |
|----|---------------------|---------|-----------|
| JP | 2012-500262 A       | 1/2012  |           |
| JP | 2015-503918 A       | 2/2015  |           |
| JP | 2015-507921 A       | 3/2015  |           |
| KR | 10-2014-0008743 A   | 1/2014  |           |
| WO | WO 2006/071794 A2   | 7/2006  |           |
| WO | 2012/131618 A1      | 10/2012 |           |
| WO | WO-2015170347 A2 *  | 11/2015 | ......... A61K 35/50 |

OTHER PUBLICATIONS

English translation of KR10-2014-0008749.*
Japanese Office Action dated Jan. 8, 2019 in Japanese Patent Application No. 2018-507615, 6 pages.
Extended European Search Report dated Mar. 7, 2019 in European Patent Application No. 16835478.5, 10 pages.
International Search Report dated Nov. 21, 2016, in PCT/KR2016/008687 filed Aug. 12, 2016.
Jui-Yu Hsieh et al., "Functional Module Analysis Reveals Differential Osteogenic and Sternness Potentials in Human Mesenchymal Stem Cells from Bone Marrow and Wharton's Jelly of Umbilical Cord", Stem Cells and Development, vol. 13, No. 12, 2010, 17 pages.
Usha Nekanti et al., "Increased Proliferation and Analysis of Differential Gene Expression in Human Wharton's Jelly-derived Mesenchymal Stromal Celis under Hypoxia", International Journal of Biological Sciences, vol. 6, 2010, 15 pages.
Korean Office Action dated Aug. 17, 2017 in Korean Application No. 10-2016-0090711.
Foreign Office Action dated Sep. 27, 2021, for KR counterpart application No. KR 10-2019-0016260.
Jui-Yu Hsieh et al., "Functional Module Analysis Reveals Differential Osteogenic and Sternness Potentials in Human Mesenchymal Stem Cells from Bone Marrow and Wharton's Jelly of Umbilical Cord," Stem Cells and Development, vol. 19, No. 12, 2010.

* cited by examiner

*Primary Examiner* — Valarie E Bertoglio
(74) *Attorney, Agent, or Firm* — United One Law Group LLC; Kongsik Kim; Jhongwoo Peck

(57) ABSTRACT

Disclosed are enhanced umbilical cord-derived adhesive stem cells, a preparation method therefor, and a use thereof. The enhanced umbilical cord-derived adhesive stem cells have an anti-inflammatory effect, a blood vessel regeneration effect, or a nerve regeneration effect, thereby being usable in a pharmaceutical composition or a cell therapeutic agent for treating or preventing various diseases.

12 Claims, 14 Drawing Sheets

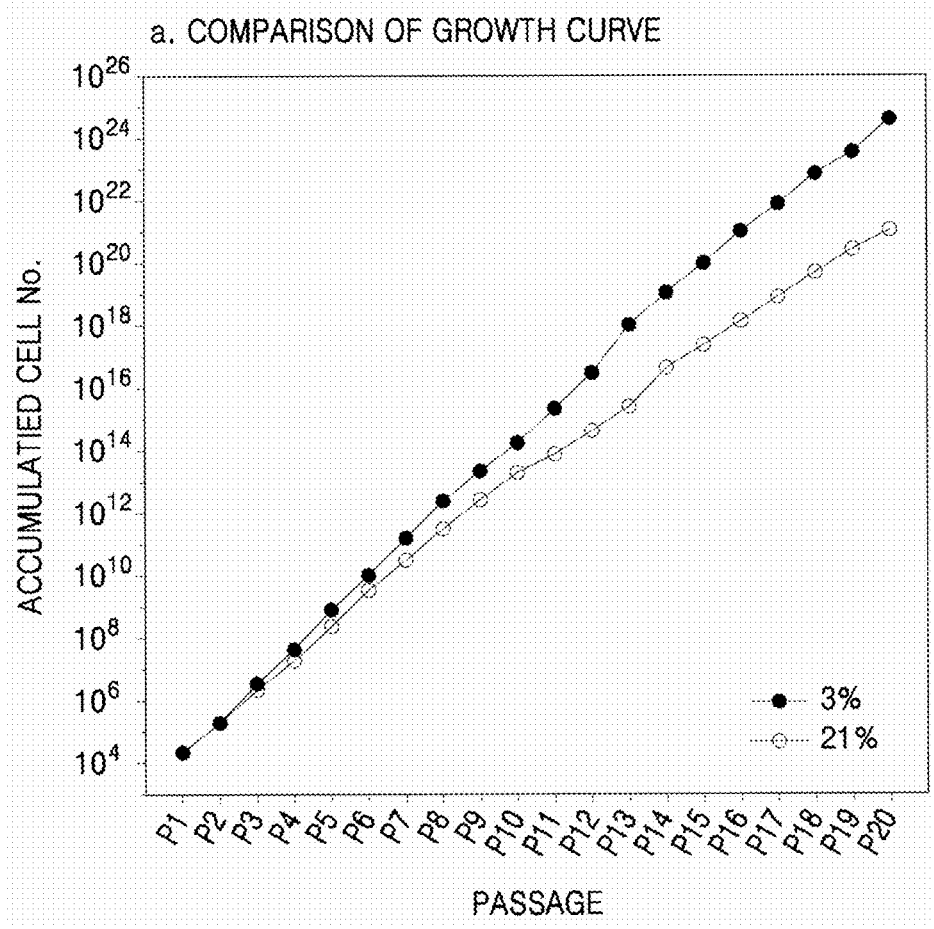

c. COMPARISON OF COLONY FORMING ABILITY

21%  3% d. COMPARISON OF CELL MIGRATION ABILITY

| CONDITION | NUMBER OF MIGRATING CELLS (cells) |
|---|---|
| 21% | 47 ± 1 |
| 3% | 73 ± 9 |

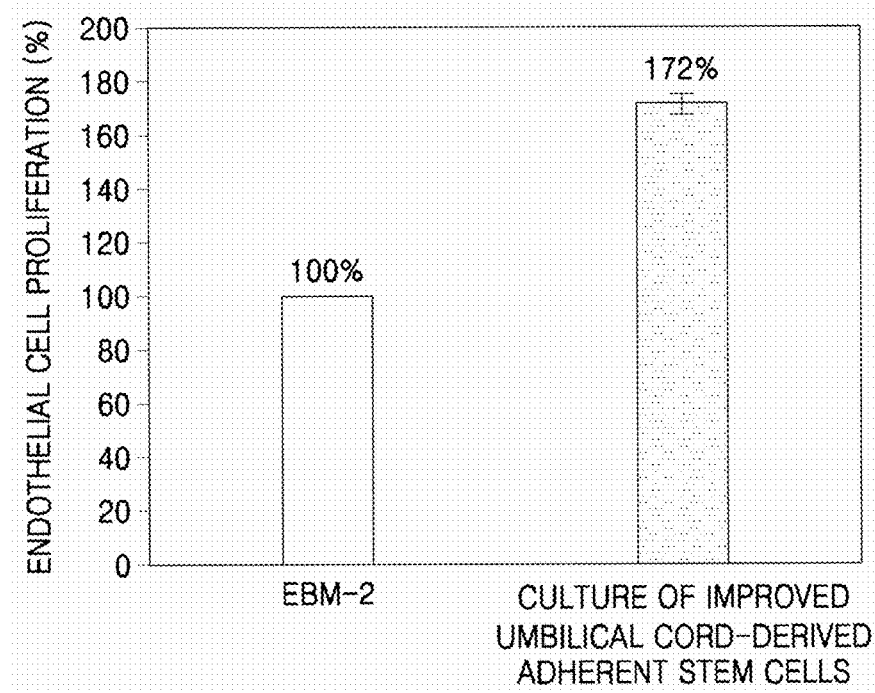

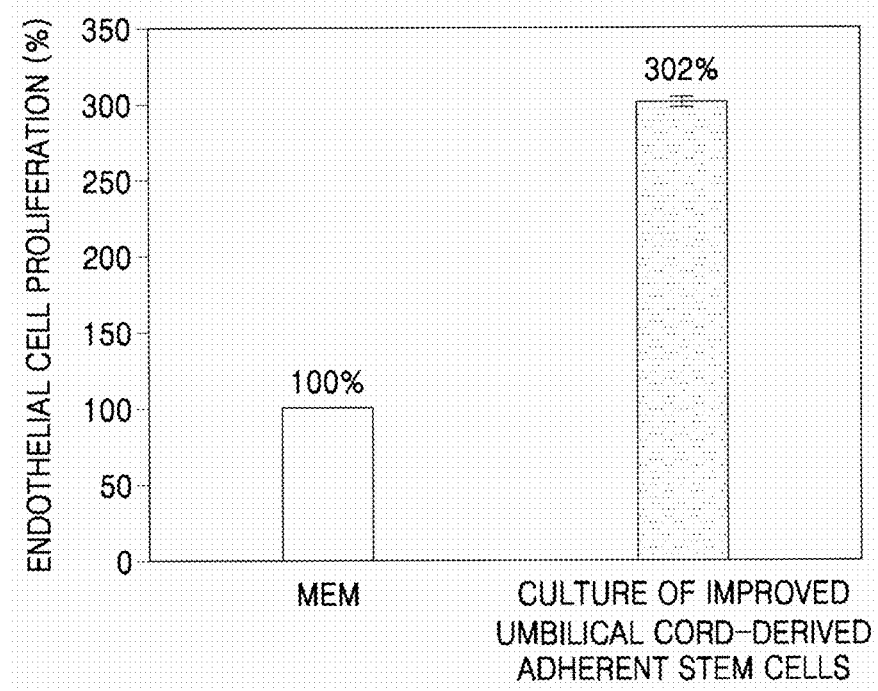

UMBILICAL CORD-DERIVED ADHERENT STEM CELLS, PREPARATION METHOD THEREFOR, AND USE THEREOF

TECHNICAL FIELD

The present disclosure relates to enhanced umbilical cord-derived adherent stem cells, a preparation method thereof, and use thereof.

BACKGROUND ART

A cell therapeutic agent is a drug used for the purpose of preventing or treating a specific disease through changing characteristics of cells by a method of proliferating or selecting cells ex vivo in order to restore functions of cells and tissues, and has recently received much attention in the fields of intractable diseases and regenerative medicines. The cell therapeutic agents may be classified into somatic cell therapeutic agents and stem cell therapeutic agents according to the degree of differentiation, and the stem cell therapeutic agents may be classified into embryonic stem cell therapeutic agents and adult stem cell therapeutic agents.

Up to now, most studies regarding adult stem cells have been conducted in the bone marrow. In some cases, stem cells isolated from adipose tissue or cord blood are cultured and administered. However, stem cells are collected from bone marrow and adipose tissue by invasive methods, and stem cells isolated from patients in adulthood or senescence have reduced differentiation and proliferation ability. Although the cord blood is easy to collect, the content of stem cells in cord blood is low.

Unlike bone marrow or adipose-derived cells, umbilical cord (UC) is non-invasive and easy to extract because it is extracted from tissues already separated from the body. Unlike embryo-derived stem cells, UC is free from ethical, issues. Recently, UC has received much attention as a useful material for intractable or regenerative medicine. Since UC-derived cells are primitive cells satisfying proliferation and differentiation abilities at the same time, there are advantages that they may be used for organ regeneration and also used after differentiation according to organ characteristics. However, UC is a tissue in which many different kinds of cells are present, and therefore, studies are required to find out optimal cells as therapeutic agents and to demonstrate new characteristics of cells that may be separated or extracted as homogeneous cell populations.

DETAILED DESCRIPTION OF THE INVENTION

An aspect provides enhanced umbilical cord-derived adherent stem cells or cell populations thereof.

Another aspect provides a method of preparing the enhanced umbilical cord-derived adherent stem cells, the method including adherent-culturing an isolated umbilical cord in a culture plate; isolating enhanced umbilical cord-derived adherent stem cells by contacting the cultured umbilical cord with a dissociation enzyme; subculturing the isolated enhanced umbilical cord-derived adherent stem cells in a medium containing fibroblast growth factor-4 (FGF-4) and heparin.

Still another aspect provides a pharmaceutical composition including the enhanced umbilical cord-derived adherent stem cells, the cell populations thereof, or a culture thereof as an active ingredient.

Technical Problem

Technical Solution

An aspect provides enhanced umbilical cord-derived adherent stem cells.

The enhanced umbilical cord-derived adherent stem cells may have one or more characteristics selected from the following (a) to (e):

a) having a high expression level of one or more selected from the group consisting of COL1A1, IGFBP4, TA LN, STC1, LRRC17, and IL33, as compared with bone marrow stem cells;

b) having a low expression level of one or more selected from the group consisting of CCND1, SERPINE1 PRNP, and CYP1B1, as compared with bone marrow stem cells;

c) maintaining, the morphology of adherent fibroblasts during subculturing;

d) having ability to differentiate into adipocytes, osteocytes, or chondrocytes; and e) having one or more surface antigen characteristics selected from the group consisting of CD200+, Tra-1-60−, CD3−, CD1a−, CD11c−, CD16−, CD86−, CD8a−, CD40−, CD141+, CD61+, CD87+, MIC A/B−, and SSEA4+.

The enhanced umbilical cord-derived adherent stem cells may further have one or more characteristics selected from the following (f) to (i):

f) having a high expression level of one or more selected from the group consisting of S100A10, BNIP3, IGFBP5, NDUFA4L2, DPYD, and SCARA3, as compared with those cultured under a normoxia condition;

g) having a low expression level of one or more selected from the group consisting of IL8, ALDH1A1, DLC1 CTHRC1, and CPA4, as compared with those cultured under a normoxia condition;

h) having a high expression level of one or more selected from the group consisting, of SNCA, DSG2, NRP2, and PLAT, as compared with bone marrow stem cells; and i) having a low expression level of one or more selected from the group consisting of TPMT, NAGK, and ANXA4, as compared with bone marrow stem cells.

The e) surface antigen characteristics of the enhanced umbilical cord-derived adherent stem cells may further include Oct4− or Nanog−. Further, CD61+ of the e) surface antigen characteristics may be a surface antigen characteristic of being overexpressed under a hypoxia condition.

The term "umbilical cord", as used herein, refers to a tube connecting the mother and the belly to allow the mammalian fetus to grow in, the placenta, and generally refers to a tissue composed of three vessels, i.e., two umbilical arteries and one umbilical vein, which are surrounded by Wharton's jelly. Therefore, in the present disclosure, the "enhanced umbilical cord-derived adherent stem cells (enhanced umbilical cord adherent stem cells)" or the "umbilical cord-derived adherent stem cells (umbilical cord adherent stem, cells)" refer to cells that are derived from the umbilical cord or the Wharton's jelly tissue of the umbilical cord and have ability to differentiate into many different cells and a characteristic of adherent growth on the surface of a culture plate.

At least about 20%, about 25%, about 30%, about 35 sA, about 40%, about 45%, about 50%, about 55%, about 60%, about 65%, about 70%, about 75%, about 80%, about 85%, about 90%, about 95%, about 98%, or about 99% of the enhanced umbilical cord-derived adherent stem cells provided in the present invention provided in the present invention may express CD200, CD141, CD61, CD87, or SSEA4 positive surface marker which is a cell marker expressed on the cell surface, and at least about 70% or less, at least about 60% or less, at least about 50% or less, at least about 40% or less, at least about 30% or less, at least about 20% or less, at least about 10% or less, at least about 5% or less, or at least about 1% or less thereof may express Oct4, Nanog, Tra-1-60, CD3, CD1a, CD11c, CD16, CD86, CD8a, MIC A/B, or CD40 negative surface marker which is a stem cell marker. The term "positive", as used herein, with respect to a stem cell marker, means that the cell marker exists in a large amount or a high concentration, as compared with that in other non-stem cells as a reference. That is, any marker is present inside or on the surface of a cell, and therefore, if a cell may be distinguished from one or more other cell types by using the marker, the cell may be positive for the marker. Further, the term "positive" means that cells have signals of higher intensity than a background intensity, for example, cells have the marker in an amount enough to be detectable in a cell-measuring device. For example, cells may be detectably labeled with CD200-specific antibodies, and when signals from these antibodies are detectably stronger than those of a control (e.g., background intensity), the cells are "CD200-F". The term "negative", as used herein, means that although antibodies specific to a particular cell surface marker are used, the marker cannot be detected, as compared with the background intensity. For example, if a cell cannot be detectably labeled with a CO3-specific antibody, the cell is "CO3-".

The above immunological characteristics may be determined by common methods known in the art to which the present disclosure pertains. For example, various methods such as flow cytometry, immunohistochemical staining, RT-PCR, etc. may be used.

The enhanced umbilical cord-derived adherent stem cells according to a specific embodiment may have a high expression level of one or more genes or proteins selected from the group consisting of COL1A1, IGFBP4, TAGLN, STC1, LRRC17, and IL33, as compared with bone marrow-derived stem cells. Specifically, the cells may have a high expression level of two or more or three or more genes or proteins selected from the group consisting of COL1A1, IGFBP4, TAGLN, STC1, LRRC17, and IL33, as compared with bone marrow-derived stem cells, or more specifically, a high expression level of all of the genes or proteins as compared with bone marrow-derived stem cells. The genes highly expressed in the enhanced umbilical cord-derived adherent stem cells according to a specific embodiment, as compared with the bone marrow-derived stem cells, may further include S100A10, SOSTM1, DSTN, DON, PHGDH, FBLN1, MFGE8 HLA-A, VASN, or KIAA1199. There are no reports about association between the above genes and the enhanced umbilical cord-derived adherent stem cells. A difference in the expression levels of the genes between the enhanced umbilical cord-derived adherent stem cells according to a specific embodiment and bone marrow-derived stem cells may be twice or higher. The difference in the expression levels may be determined by, for example, comparing the gene expression levels at an mRNA level. Further, the difference in the expression levels may be determined by, for example, microarray analysis.

Further, the enhanced umbilical cord-derived adherent stem cells according to a specific embodiment may have a low expression level of one or more genes or proteins selected from the group consisting of CCND1, SERPINE1, PRNP, and CYP1B1, as compared with bone marrow-derived stem cells. Specifically, the cells may have a low expression level of two or more or three or more genes or proteins selected from the group consisting of COND1, SERPINE1, PRNP and CYP1B1, as compared with bone marrow-derived stem cells, or more specifically, a low expression level of all of the genes or proteins, as compared with bone marrow-derived stem cells. The genes or proteins poorly expressed in the enhanced umbilical cord-derived adherent stem cells according to a specific embodiment, as compared with the bone marrow-derived stem cells, may include MTA2A, TM4SF1, HIST1H4C, and NME1. There are no reports about association between the above genes or proteins and the enhanced umbilical, cord-derived adherent stem cells. A difference in the expression levels of the genes or the proteins between the enhanced umbilical cord-derived adherent stem cells according to a specific embodiment and bone marrow-derived stem cells may be twice or higher. The difference in the expression levels may be determined by, for example, comparing the gene expression levels at an mRNA level. Further, the difference in the expression levels may be determined by, for example, microarray analysis.

Further, the enhanced umbilical cord-derived adherent stem cells may have a fibroblast morphology under subculturing. In a specific embodiment, the cells may have the property of cells requiring adhesion to the surface to grow in vitro, and may exhibit a spindle-shaped fibroblast-specific morphology.

In another specific embodiment, the enhanced umbilical cord-derived adherent stem cells may have colony-forming ability. The cells may have high colony-forming ability, as compared with those cultured under a normoxia condition.

Further, the enhanced umbilical cord-derived adherent stem cells may differentiate into adipocytes, osteocytes, chondrocytes, etc. The cells may be induced to differentiate into particular cell lineages, for example, adipocytes, chondrocytes, osteoblasts, hematopoietic cells, myocytes, vascular cells, neurons, or hepatocytes.

The term "differentiation", as used herein, refers to a process by which cells become more specialized in structure or function during cell growth through division and proliferation, i.e., a process by which cells, tissues, etc. of a living body change in shape or function in order to perform the given task. Determination of differentiation into particular cell lineages may be accomplished by methods well-known in the art, and differentiation into particular cells may be induced through the known methods. Further, the differentiation may be confirmed by measuring changes in cell surface markers (e.g., staining cells with tissue-specific or cell-marker specific antibodies) and morphology using techniques such as flow cytometry or immunocytochemistry, or by examining the morphology of cells using an optical microscope or confocal, microscope, or by measuring changes in gene expression using techniques well known in the art, such as PCR and gene-expression profiling.

Further, the enhanced, umbilical cord-derived adherent stem cells may secrete IL-6, IL-8, G-CSF, GM-CSF, MCP-3, VEGF, GRO, IFNγ, IL-1a, IL-1b, IL-1ra, IL-3, IL-4, IL-7, IL-9, IL-12(p40), IL12(P70), IL-13, IL-14, IFNα2, MDC, sIL-2Ra, Eotaxin, Flt-3 ligand, MCP-1, MIP-1a, MIP1b, RANTE, fractalkine, IP-10, EGF, FGF-2, IGF-1 SR, EpCAM, 1GFBP3, or a combination of these proteins. Further, the enhanced umbilical cord-derived adherent stem cells may secrete, for example, two or more, three or more, four or more, five or more, six or more, seven or more, eight or more, nine or more, ten or more selected from the group consisting of IL-6, IL-8, G-CSF, GM-CSF, MCP-3, VEGF, and GRO, and all of the proteins.

Further, the enhanced umbilical cord-derived adherent stem cells cultured under a hypoxia condition may have increased expression level of one or more genes or proteins selected from the group consisting of S100A10, BNIP3, IGFBP5, PGK1, TPI1, DCN, PGM1, PFKFB3, LOC644774, MME, MIR1978, SLC2A3, BHLHB2, BNIP3L, IGFBP5, NDUFA4L2, DPYD, and SCARA3, as compared with those cultured under a normoxia condition. Specifically, the enhanced umbilical cord-derived adherent stem cells cultured under a hypoxia condition may have increased expression level of two or more, three or more, four or more, five or more, or six or more genes or proteins selected from the group consisting of S100A10, BNIP3, IGFBP5, PGK1, TPI1, DCN, PGM1, PFKFB3, LOC644774, MME, MIR1978, SLC2A3, BHLHB2, BNIP3L, IGFBP5, NDUFA4L2, DPYD, and SCARA3, or increased expression level of all of the genes or proteins, as compared with those cultured under a normoxia condition. There are no reports about association between the above genes or proteins and the enhanced umbilical cord-derived adherent stem cells. A difference in the expression levels may be twice or higher. The difference in the expression levels may be determined by, for example, comparing the gene and protein expression levels at an mRNA level or at a protein level. Further, the difference in the expression levels may be determined by, for example, microarray analysis and proteomic analysis.

Further, the enhanced umbilical cord-derived adherent stem, cells cultured under a hypoxia condition may have decreased expression level of one or more ₋genes or proteins selected from the group consisting of IL8, ALDH1A1, NQO1, DLC1, CTHRC1, and CPA4, as compared with those cultured under a normoxia condition. Specifically, the enhanced umbilical cord-derived adherent stem cells cultured under a hypoxia condition may have decreased expression level of two or more or three or more genes or proteins selected from the group consisting of IL8, ALDH1A1, NQO1, DLC1, CTHRC1 and CPA4, or decreased expression level of all of the genes or proteins, as compared with those cultured under a normoxia condition. There are no reports about association between the above genes or proteins and the enhanced umbilical cord-derived adherent stem cells. A difference in the expression levels may be twice or higher. The difference in the expression levels may be determined by, for example, comparing the gene and protein expression levels at an mRNA level or at a protein level. Further, the difference in the expression levels may be determined by, for example, microarray analysis and proteomic analysis.

Another aspect provides cell populations of enhanced umbilical cord-derived adherent stem cells.

The umbilical cord-derived adherent stem cells are the same as described above.

Still another aspect provides a method of preparing the enhanced umbilical cord-derived adherent stem cells, the method including adherent-culturing an, isolated umbilical cord in a culture plate; isolating enhanced umbilical cord-derived adherent stem cells by contacting the cultured umbilical cord with a dissociation enzyme; subculturing the isolated enhanced umbilical cord-derived adherent stem cells in a medium containing fibroblast growth factor-4 (FGF-4) and heparin.

The umbilical cord may be an umbilical cord which is separated from a heathy mother (e.g., HIV, IHCV, HBV-negative mother) after delivery. That is, the "separated umbilical cord" may refer to an umbilical cord separated from the body of the mother after delivery. The separated umbilical cord may be stored in a sterile container with ice immediately after being separated.

A method of separating and obtaining the umbilical cord from the placenta may include, for example, separating the umbilical cord from the separated placenta; removing external blood of the separated umbilical cord; removing arteries and veins from the blood-removed umbilical cord; and/or cutting the umbilical cord, from which the artery and vein are removed, in a predetermined size (e.g., 1 mm to 20 mm). The removing of the blood may be performed by using Ca/Mg-free DPBS, or gentamycin-containing Ca/Mg-free DPBS.

Next, stem cells may be isolated from the umbilical cord which is cut in a small size (e.g., separated umbilical cord). The isolating of the enhanced umbilical cord-derived adherent stem cells may include adherent-culturing the separated umbilical cord in a culture plate for 5 days to 20 days, for example, 10 days to 20 days, for example, for 10 days to 15 days; confirming that cells extend from the cultured umbilical cord tissue; and/or treating the umbilical cord tissue with a dissociation enzyme.

The dissociation enzyme may include collagenase. The collagenase may refer to an enzyme that cleaves peptide bonds of collagen, and may include collagenase type I, type II, type III, type IV, or a combination thereof. Further, the dissociation enzyme may include collagenase of 5 U/ml to 30 U/ml, for example, 5 U/ml to 25 U/ml, 10 U/ml to 25 U/ml, or 20 U/ml. Further, the dissociation enzyme may include trypsin, and/or dispase. Further, a solution including the dissociation enzyme may include water, saline, for example, HBSS (Hank's Balanced Salt Solution) containing collagenase, trypsin, and/or dispase. Further, a treatment time of the dissociation enzyme may be, for example, 1 hour to 20 hours, 2 hours to 10 hours, 4 hours to 9 hours, or 5 hours to 6 hours.

In a specific embodiment, reaction between the tissue and the dissociation enzyme may be allowed under shaking, and the shaking may be performed, for example, at about 20° C. to about 40° C., about 30° C. to about 40° C., or about 35° C. to about 40° C., for example, at about 37° C., for about 5 minutes to about 60 minutes or about 10 minutes to about 30 minutes, for example, for about 10 minutes to about 30 minutes twice.

Additionally, after reaction of the tissue and the dissociation enzyme, a process of inactivating the dissociation enzyme may be further performed, and for example, the enzymatic reaction may be terminated by adding FBS. Further, a method of isolating tissue cells, for example, enhanced umbilical cord-derived adherent stem cells from the enzyme reaction solution may be performed by a common method known in the art. For example, after centrifugation, cells may be isolated by using a cell strainer.

The term "isolation of the enhanced umbilical cord-derived adherent stem cells", as used herein, means removal of at least 20%, 30%, 40%, 50%, 60% 70%, 80%, 90%, 95% or 99% of cells normally associated with the stem cells in an untreated mammalian umbilical cord. Cell populations containing stem cells obtained from one organ may be said to "be isolated", when other cells normally associated with the stem cells in the untreated organ is less than 50% of the entire cells.

Next, subculturing may be performed by taking the isolated enhanced umbilical cord-derived adherent stem cells as P0.

The subculturing may further include treating animal component-free (ACF) recombinant enzyme before cell transplantation for subculturing. The term "animal component-free enzyme", as used herein, means that the enzyme is originated from a non-animal, which means that the enzyme is not purified from an animal supply source. The animal component-free enzyme may be originated from recombination, for example, originated from bacteria, yeasts, or plants. The enzyme originated from recombination may mean any enzyme produced by recombinant DNA technology including use of microorganisms, for example, bacteria, viruses, yeasts, plants, etc. The enzyme may be animal component-free recombinant trypsin, for example, recombinant trypsin produced in corn. The animal component-free recombinant trypsin is commercially available, and for example, it may be TrypLE™ Select (GIBCO Invitrogen), TrypLE™ Express (GIBCO Invitrogen), TrypZean™ (Sigma Aldrich), or Recombinant Trypsin solution™ (Biological Industries).

The subculturing may include culturing the cells in a stem cell culture medium, for example, in a medium supplemented with fibroblast growth factor (FGF-4) and heparin. A concentration of FGF-4 in the medium may be about 10 ng/ml to about 40 ng/ml, or about 20 ng/ml to about 30 mg/ml, for example, 25 ng/ml. A concentration of heparin in the medium may be about 0.5 μg/ml to about 2 μg/ml, or about 0.5 μg/ml to about 1.5 μg/ml, for example, about 1 μg/ml. The medium may further include, for example, fetal bovine serum and antibiotics (e.g., penicillin, streptomycin, gentamycin, etc.). In a specific embodiment, a CS-CM medium supplemented with 10% fetal bovine serum, 50 μg/ml of gentamycin, 1 μg/ml of heparin, and 25 ng/ml of FGF-4 may be used. The subculturing may be performed at about 20° C. to about 40° C., about 30° C. to about 40° C., or about 35° C. to about 40° C., for example, at about 37° C., and a culture time for each subculturing may be, for example, 2 days to 7 days, or 3 days to 5 days.

In the method of preparing the enhanced umbilical cord-derived adherent stem cells according to a specific embodiment, a passage number of the subculturing is not particularly limited, and the passage number may be appropriately selected according to the desired number of proliferating cells. Commonly, the passage number may be at least 1 passage or more, or 10 passages or more. For example, 1 passage to 20 passages or 3 passages to 15 passages may be performed to obtain the clinically required cumulative number of proliferating cells.

Further, upon subculturing, treatment of the animal component-free recombinant enzyme may be also additionally performed as described above. That is, at every stage of subculturing before subculturing of the cells to the next stage, the cells were treated with the animal component-free recombinant enzyme and harvested to increase purity of the cells. For example, the animal component-free recombinant enzyme may be treated before transferring the cells for P2 at the stage from P1 to P2.

The subculturing may be subculturing under a hypoxia condition at a lower oxygen level than the normoxia condition of 21%. The term "hypoxia" means an oxygen partial pressure lower than an oxygen partial pressure of 21% which is a general normoxia condition. The hypoxia condition may be a condition having an oxygen partial pressure of 1% to 15%, 1% to 12%, 1% to 10%, or 1% to 5%, for example, 1%, 2%, 3%, 4%, 5%, 6%, 7%, 8%, or 9%.

In a specific embodiment, when the cells are subcultured under the hypoxia condition, an expression level of one or more selected from the group consisting of S100A10, BNIP3, IGFBP5, PGK1, TPI1, DCN, PGM1, PFKFB3, LOC644774, MME, MIR1978, SLC2A3, BHLHB2, BNIP3L, IGFBP5, NDUFA4L2, DPYD, and SCARA3 may be increased, or an expression level of one or more selected from the group consisting of IL8, ALDH1A1, NQO1, DLC1, CTHRC1, and CPA4 may be decreased, as compared with those subcultured in the normoxia condition.

The enhanced umbilical cord-derived adherent stem cells prepared by the above preparation method may have the above-described characteristics, and for example, the prepared enhanced umbilical cord-derived adherent stem cells may have one or more characteristics selected from the following (a) to (e):

a) having a high expression level of one or more selected from the group consisting of COL1A1, IGFBP4, TAGLN, STC1, LRRC17 and IL33, as compared with bone marrow stem cells;

b) having a low expression level of one or more selected from the group consisting of CCND1, SERPINE1, PRNP, and CYP1B1, as compared with bone marrow stem cells:

c) maintaining the morphology of adherent fibroblasts during subculturing;

d) having ability to differentiate into adipocytes, osteocytes, or chondrocytes; and e) having one or more surface antigen characteristics selected from the group consisting of CD200+, Tra-1-60−, CD3−, CD1a−, CD11c−, CD16−, CD86−, CD8a−, CD40−, CD141+, CD61+, CD87+, MIC A/B−, and SSEA4+.

The enhanced umbilical cord-derived adherent stem cells may further have one or more characteristics selected from the following (f) to (i):

f) having a high expression level of one or more selected from the group consisting of S100A10, BNIP3, IGFBP5, NDUFA4L2, DPYD, and SCARA3, as compared with those under a normoxia condition;

g) having a low expression level of one or more selected from the group consisting of IL8, ALDH1A1, DLC1, CTHRC1, and CPA4, as compared with those under a normoxia condition;

h) having a high expression level of one or more selected from the group consisting of SNCA, DSG2, NRP2, and PLAT, as compared with bone marrow stem cells; and i) having a low expression level of one or more selected from the group consisting of TPMT, NAGK, and ANXA4, as compared with bone marrow stem cells.

The e) surface antigen characteristics of the enhanced umbilical cord-derived adherent stem cells may further include Oct4− or Nanog−. Further, CD61+ of the e) surface antigen characteristics may be a surface antigen characteristic of being, overexpressed under a hypoxia condition.

Still another aspect provides a cell therapeutic agent, or a pharmaceutical composition or agent including the enhanced umbilical cord-derived adherent stem cells, the cell populations thereof, or a culture thereof as an active ingredient.

Still another aspect provides use of the enhanced umbilical cord-derived adherent stem cells, the cell populations thereof, or the culture thereof for the preparation of the cell therapeutic agent, or the pharmaceutical composition or agent.

For example, provided is the cell therapeutic agent, or the pharmaceutical composition or agent including the enhanced umbilical cord-derived adherent stem cells having one or more characteristics selected from the following (a) to (e), or the cell populations thereof:

a) having a high expression level of one or more selected from the group consisting of COL1A1, IGFBP4, TAGLN, STC1, LRRC17, and IL33, as compared with bone marrow stem cells;

b) having a low expression level of one or more selected from the group consisting of CCND1, SERPINE1. PRNP, and CYP1B1, as compared with bone marrow stem cells;

c) maintaining, the morphology of adherent fibroblasts during subculturing;

d) having ability to differentiate into adipocytes, osteocytes, or chondrocytes; and e) having one or more surface antigen characteristics selected from the group consisting of CD200+, Tra-1-60−, CD3−, CD1a−, CD11c−, CD16−, CD86−, CD8a−, CD40−, CD141+, C061+, CD87+, MIC A/B−, and SSEA4+.

The enhanced umbilical cord-derived adherent stem cells may further have one or more characteristics selected from the following (f) to (i):

f) having a high expression level of one or more selected from the group consisting of S100A10, BNIP3, 1GFBP5, NDUFA4L2, DPYD, and SCARA3, as compared with those under a normoxia condition;

g) having a low expression level of one or more selected from the group consisting of IL8, ALDH1A1, DLC1, CTHRC1, and CPA4, as compared with those under a normoxia condition;

h) having a high expression level of one or more selected from the group consisting of SNCA, DSG2, NRP2, and PLAT, as compared with bone marrow stem cells; and i) having a low expression level of one or more selected from the group consisting of TPMT, NAGK, and ANXA4, as compared with bone marrow stem cells.

Further, the above aspect includes a pharmaceutical composition including the culture of the enhanced umbilical cord-derived adherent stem cells. Further, provided is, for example, a pharmaceutical composition for treating or preventing inflammatory diseases, ischemic diseases, and/or neurodegenerative diseases, the pharmaceutical composition including the enhanced umbilical cord-derived adherent stem cells, the cell populations thereof, or the culture thereof as an active ingredient.

Still another aspect provides use of the enhanced umbilical cord-derived adherent stem cells, the cell populations thereof, or the culture thereof for the preparation of a drug for treating or preventing a disease, for example, inflammatory diseases, ischemic diseases, and/or neurodegenerative diseases.

Still another aspect provides a method of treating or preventing a disease, for example, inflammatory diseases, ischemic diseases, and/or neurodegenerative diseases, the method including administering the enhanced umbilical cord-derived adherent stem cells, the cell populations thereof, or the culture thereof as an active ingredient to a subject in need thereof.

The enhanced umbilical cord-derived adherent stem cells are the same as described above.

The enhanced umbilical cord-derived adherent stem cells according to a specific embodiment may release proteins (e.g., IL-6, IL-8, G-CSF, GM-CSF, MCP-3, VEGF, or GRO) that are advantageous for disease treatment as described above and may have a remarkable ability to migrate into damaged tissues, as well as anti-inflammatory, vascular regeneration, and nerve regeneration effects. Therefore, the enhanced umbilical cord-derived adherent stern cells may be usefully applied to a cell therapeutic agent or a pharmaceutical composition for the prevention or treatment of various diseases including inflammatory diseases, ischemic diseases, and/or neurodegenerative diseases.

Examples of the diseases may include inflammatory diseases, ischemic diseases, and/or neurodegenerative diseases. Examples of the inflammatory diseases may include bronchitis, gastritis, arteriosclerosis, arthritis, inflammatory bowel disease (IBD), hepatitis, cholecystitis, fungal infections, gastric ulcer, asthma, atopic dermatitis, tendinitis or nephritis. Examples of the ischemic diseases may include ischemic stroke, myocardial infarction, ischemic heart disease, ischemic brain disease, ischemic heart failure, ischemic enteritis, ischemic vascular disease, ischemic eye disease, ischemic retinopathy, ischemic glaucoma, ischemic renal failure, or ischemic limb disease. The "ischemic stroke" or "stroke" may refer to a disease caused by necrotic brain tissues or cells resulting from cerebral blood flow reduction for a certain period of time or longer, and may be used interchangeably with "cerebral infarction".

Examples of the neurodegenerative diseases may include spinal cord injury, multiple sclerosis, Alzheimer's disease, frontotemporal dementia, progressive supranuclear palsy, corticobasal degeneration, Pick's disease, or dementia pugilistica, (DP).

A dosage of the cell therapeutic agent or the pharmaceutical composition according to a specific embodiment may be $1.0 \times 10^3$ to $1.0 \times 10^{10}$ cells/kg (body weight) or subject, or $1.0 \times 10^7$ to $1.0 \times 10^8$ cells/kg (body weight) or subject, based on the enhanced umbilical cord-derived adherent stem cells. However, the dosage may be variously prescribed depending on various factors such as a formulation method, an administration mode, a patient's age, body weight, sex, disease conditions, diet, an administration time, an administration route, an excretion rate, and reaction sensitivity, and those skilled in the art may appropriately adjust the dosage, considering these factors. Administration frequency may be once or twice or more within the clinically allowable range of side effects, and administration may be given to one site or two or more sites. The dosage per kg or per subject for non-human animals may be the same as that for humans, or may be converted from the above-described dosage, for example, based on a volume ratio (e.g., mean, value) between organs (heart, etc.) of the human and animal subjects. Animals to be treated according to a specific embodiment may be exemplified by humans and other desired mammals, and specifically, may include humans, monkeys, mice, rats, rabbits, sheep, cows, dogs horses, pigs, etc.

The cell therapeutic agent or the pharmaceutical composition according to a specific embodiment may include the enhanced umbilical cord-derived adherent stem cells and pharmaceutically acceptable carriers and/or additives as an active ingredient, and for example, may include sterilized water, physiological saline, a standard buffer (e.g., phosphoric acid, citric acid, or other organic acids), a stabilizer, a salt, an antioxidant (e.g., ascorbic acid, etc.), a surfactant, a suspending agent, an isotonic agent, a preservative, etc. For local administration, the cell therapeutic agent or the pharmaceutical composition is preferably combined with an organic substance such as a biopolymer, an inorganic substance such as hydroxyapatite, specifically, collagen matrix, a polymer or copolymer of polylactic acid, a polymer or copolymer of polyethylene glycol, and chemical derivatives thereof. When the cell therapeutic agent or the pharmaceutical composition according to a specific embodiment is prepared in an injectable formulation, cell, populations may be dissolved in a pharmaceutically acceptable carrier or may be frozen in a solution state in which the cell populations are dissolved.

The enhanced umbilical cord-derived adherent stem cells according to a specific embodiment may be used in various kinds of therapeutic protocols for enhancing, treating, or replacing an organ or a tissue of the body by engraftment, transplantation, or injection of desired cell populations, for example, stem cells or stem cell-derived cell populations. The enhanced umbilical cord-derived adherent stem cells may be used to replace or enhance existing tissues so that the tissue may become a newly altered tissue or may be bound with a biological tissue or structure.

Further, in therapeutic protocols of using stem cells derived from tissues other than the umbilical cord, the stem cell may be replace by the enhanced umbilical cord-derived adherent stem cells of the present disclosure.

The cell therapeutic agent or the pharmaceutical composition according to a specific embodiment may include, if necessary, a suspending agent, a solubilizing aid, a stabilizer, an isotonic agent, a preservative, an adsorption inhibitor, a surfactant, a diluent, an excipient, a pH adjuster, an analgesic agent, a buffer, a reducing agent, an antioxidant, etc., depending upon the administration mode and formulation. In addition to those described above, pharmaceutically acceptable carriers and agents suitable in the present disclosure are described in detail in a literature [Remington's Pharmaceutical Sciences, 19$^{th}$ ed., 1995].

The cell therapeutic agent or the pharmaceutical composition according to a specific embodiment may be formulated in a unit dosage form or into a multidose container using a pharmaceutically acceptable carrier and/or excipient according to a method that may be easily carried out by those skilled in the art to which the present disclosure pertains. In this regard, the formulation may be in a form of a solution, a suspension, or an emulsion in an oily or aqueous medium, a powder, granules, a tablet, or a capsule. Further, the cell therapeutic agent may be prepared as an injectable formulation. In this case, common ingredients known for formulation may be used, and the formulation may be prepared by a common method.

Advantageous Effects of the Invention

Enhanced umbilical cord-derived adherent stem cells according to an aspect may have anti-inflammatory, vascular regeneration, and nerve regeneration effects, thereby being usefully applied to a pharmaceutical composition or a cell therapeutic agent, for treating or preventing various diseases.

A method of preparing the enhanced umbilical cord-derived adherent stem cells according to another aspect may be used to increase purity, yield, and proliferation rate of stem cells from an umbilical cord tissue.

DESCRIPTION OF THE DRAWINGS

FIG. 7B shows results of analyzing, a vascular regeneration effect of the enhanced umbilical cord-derived adherent stem cells according to a specific embodiment; and FIG. 7C shows results of analyzing a nerve regeneration effect of the enhanced umbilical cord-derived adherent stem cells according to a specific embodiment.

MODE OF THE INVENTION

Hereinafter, the present invention will be described in more detail. However, these Examples are for illustrative purposes only, and the scope of the present invention is not intended to be limited by these Examples.

EXAMPLE 1

Preparation of Enhanced Umbilical Cord-derived Adherent Stem Cells, Characterization thereof, and Analysis of Anti-inflammatory, Nerve Regeneration, Vascular Regeneration Effects 1. Preparation of Enhanced Umbilical Cord-derived Adherent Stem Cells and Comparison according to Culture Method (1.1) Isolation and Culture of Enhanced Umbilical Cord-derived Adherent Stem Cells 1

After an informed consent form was signed by a healthy woman who had normally delivered and was directly given information about the research, an umbilical cord was separated from a placental tissue collected during normal placenta delivery. The removed umbilical cord was washed with Ca/Mg free DPBS twice or five times to remove blood, and then two arteries and one vein were removed without removing an external amnion layer, and then the umbilical cord was cut in a size of 1 mm to 5 mm. Then, the umbilical cord was subjected to adherent culture in a culture plate for 10 days to 15 days. After confirming that cells extended from the cultured tissues, 200 U/ml of collagenase I was treated for 5 hours to 6 hours to isolate enhanced umbilical cord-derived adherent stem cells. Before and after treatment of collagenase I, cell morphology was examined under an optical microscope at 40×, 100× magnification in order to confirm that cells extended from the umbilical cord adherent tissue, and the results are shown in FIG. 1A.

Figure 1A:
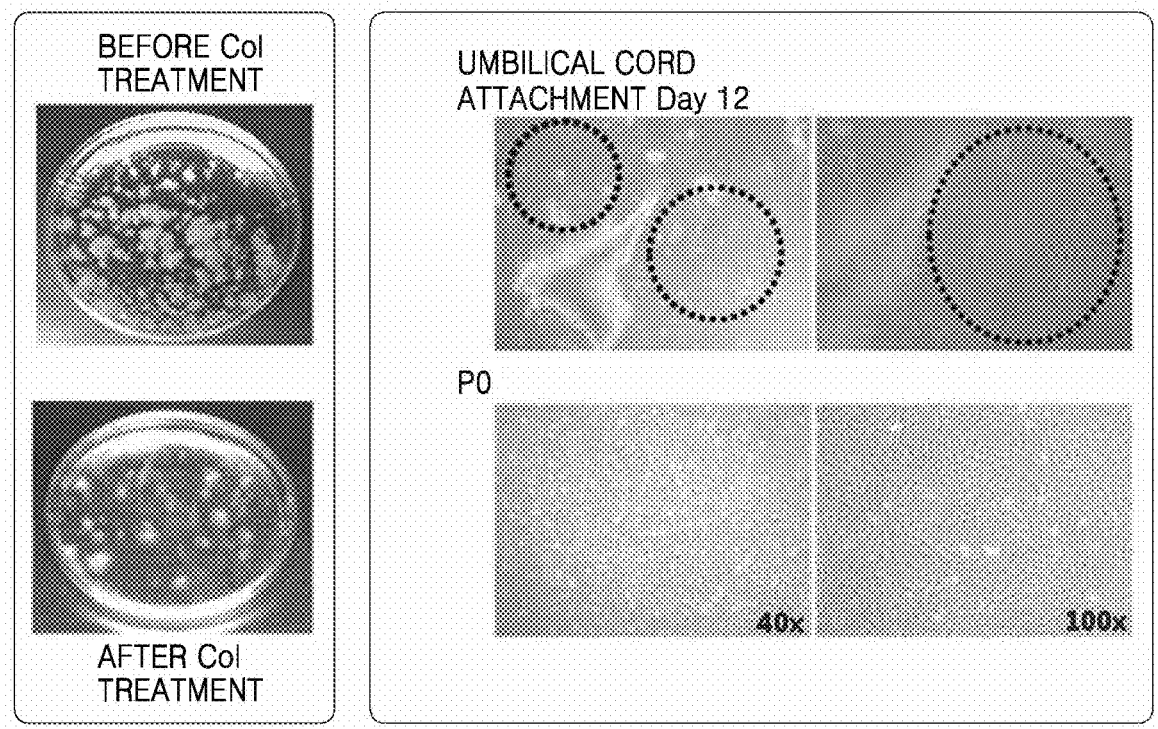
FIG. 1A shows cell morphology before and after treatment of a dissociation enzyme in isolation of enhanced umbilical cord-derived adherent stem cells according to a specific embodiment.

FIG. 1A shows cell morphology before and after treatment of a dissociation enzyme in, the isolation of enhanced umbilical cord-derived adherent stem cells according to a specific embodiment.

As shown FIG. 1A, after treatment of collagenase I vehicle is the dissociation enzyme, homogeneous cell morphology was observed.

Thereafter, the isolated cells as P0 were cultured in MEM alpha GlutaMAX (CS-CM medium) containing 25 ng/ml FGF4, 1 μg/ml heparin, and 10% FBS at 37° C. under a hypoxia culture condition ($O_2$ 3%). Thereafter, the CS-CM medium was replaced every 3 days to 4 days to remove cells which did not adhere to the bottom of flask. Cells were subcultured by treatment with TrypLE (Invitrogen), which is an animal component-free (ACF) recombinant enzyme, in a 37° C. incubator for a short time (3 minutes) at a first passage.

(1.2) Isolation and Culture of Enhanced Umbilical Cord-derived Adherent Stem Cells 2

Enhanced umbilical cord-derived adherent stem cells were isolated and cultured in the same manner as in (1.1), except that the treatment of collagenase I was performed before attaching the umbilical cord to the culture plate in (1.1).

(1.3) Isolation and Culture of Enhanced Umbilical Cord-derived Adherent Stem Cells 3

Enhanced umbilical cord-derived adherent stem cells were isolated and cultured in the same manner as in (1.1), except that the stem cells isolated in (1.1) were cultured in a normoxia condition ($O_2$ 21%).

(1.4) Comparison Analysis according to Treatment Time of Dissociation Enzyme

To compare cell recovery rates of the stem cells isolated in (1.1) and (1.2), the stem cells isolated in (1.2) and (1.1) were named G1 and G2, respectively. The cell morphology thereof were examined under an optical microscope at 40×, 100× magnification and the results are shown in FIG. 1B.

Figure 1B:
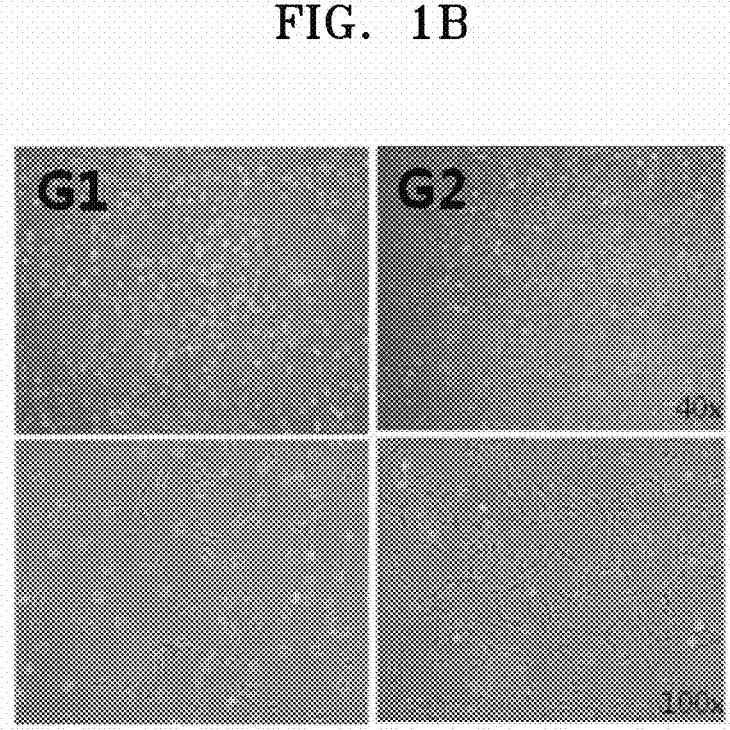
FIG. 1B shows cell morphology according to treatment time of the dissociation enzyme in isolation of the enhanced umbilical cord-derived adherent stem cells according to a specific embodiment, G1: Col I-treated group, G2: Col I-treated group after tissue attachment.

FIG. 1B shows cell morphology according to treatment time of the dissociation enzyme in the isolation of the enhanced umbilical cord-derived adherent stem cells according to a specific embodiment.

Further, the tissue weights of G1 and G2, the number of cells after treatment of the dissociation enzyme and the number of cells (P0) were compared.

TABLE 1

| Group | | Tissue weight (g) | Number of cells after treatment of dissociation enzyme | Number of cells (P0) |
|---|---|---|---|---|
| G1 | Col I-treated group | 2.71 | $3.1 \times 10^5$ | $3.02 \times 10^5$ |
| G2 | Col I-treated group after tissue attachment | 3.14 | — | $3.45 \times 10^5$ |

As shown in FIG. 1B and Table 1, when the dissociation enzyme was treated before culture of umbilical cord, most cells had cobblestone-shaped morphology and proliferated slowly to show a low cell yield. When the dissociation enzyme was treated after culture of umbilical cord, cells had homogeneous cell morphology and proliferated rapidly to show a high cell yield.

(1.5) Comparison Analysis according to Hypoxia and Normoxia Conditions

Figure 2B:
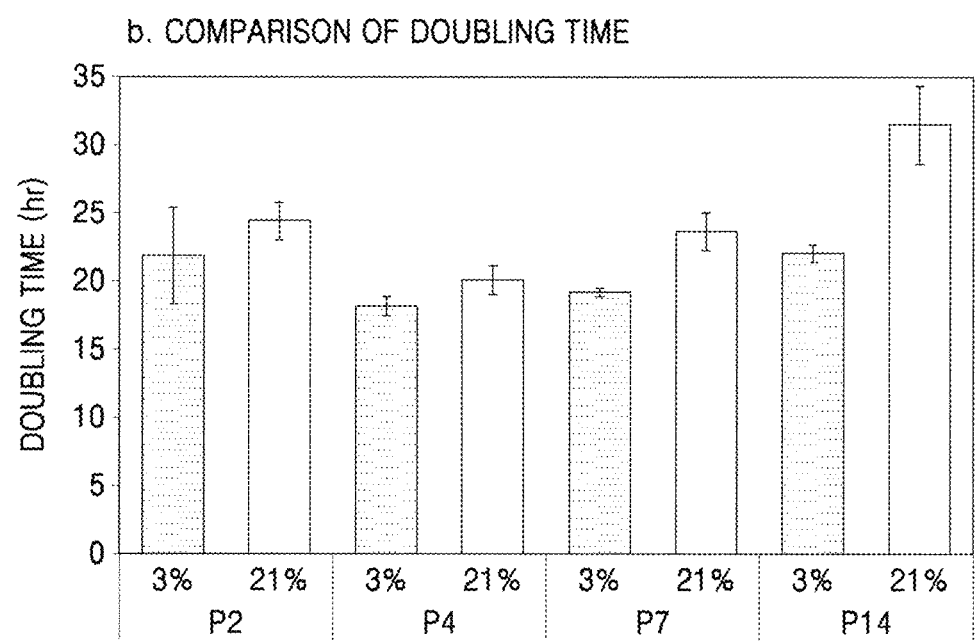
FIG. 2 shows comparison between a hypoxia condition and a normoxia condition in culturing of the enhanced umbilical cord-derived adherent stem cells according to a specific embodiment: low oxygen partial pressure (3% $O_2$), 21%: normal oxygen partial pressure (21% $O_2$)

To compare growth curves and doubling times of adherent cells subcultured for 1 passage to 20 passages (P1 to P20) under a hypoxia condition of (1.1) and a normoxia condition (1.2), each same number of cells was seeded in a 6-well plate, and cells were harvested when they occupied 70%-80% of the bottom area of the plate. Thereafter, 10 µl of the sample was mixed with 10 µl of trypan blue, and 10 µl thereof was injected into one measurement section of a hemocytometer. The number of cells was counted by using an automated cell counter. At this time, time was also recorded to calculate the doubling time. The doubling time, which is a time it takes for a cell to double, was calculated using the total number of cells and the time when the number was measured. The results are shown in FIGS. 2A and 2B.

Figure 2C:
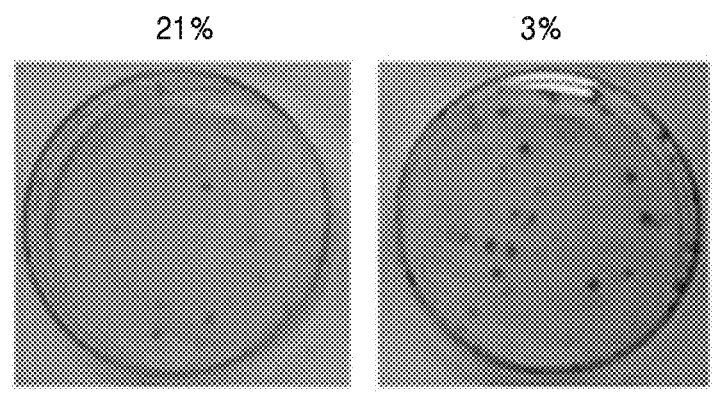
Figure 2C:
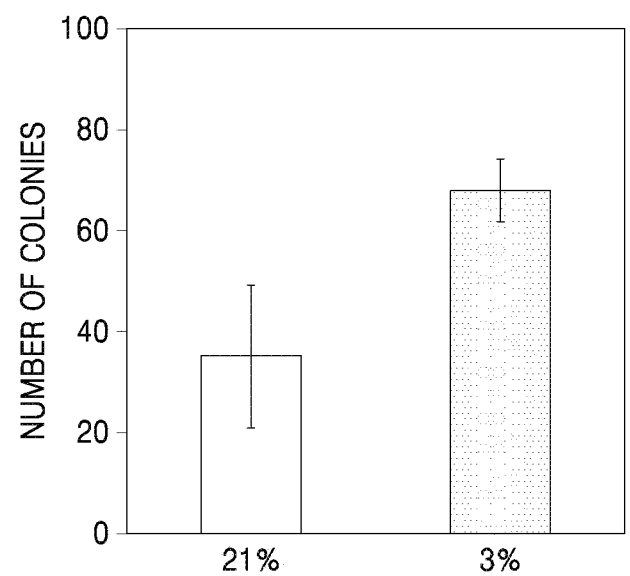

Further, to analyze colony forming ability of the cells, 150 cells per dish was spread on a 100 mm culture dish, and cultured in 12 ml of culture medium for 10 days to 14 days. Cell colony formation was examined under a microscope. Next, the cells were washed with DPBS, and 2 ml to 3 ml of a mixed solution of glutaraldehyde and crystal violet was added to cells in the dish and stained for 30 minutes. The cells were carefully washed with sterile water and the number of colonies was counted under a microscope, and presented as mean values to analyze results. The results are shown in FIG. 2C.

Figure 2D:
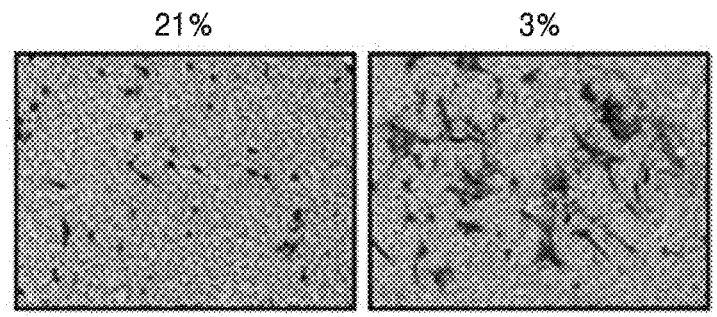
Figure 2D:
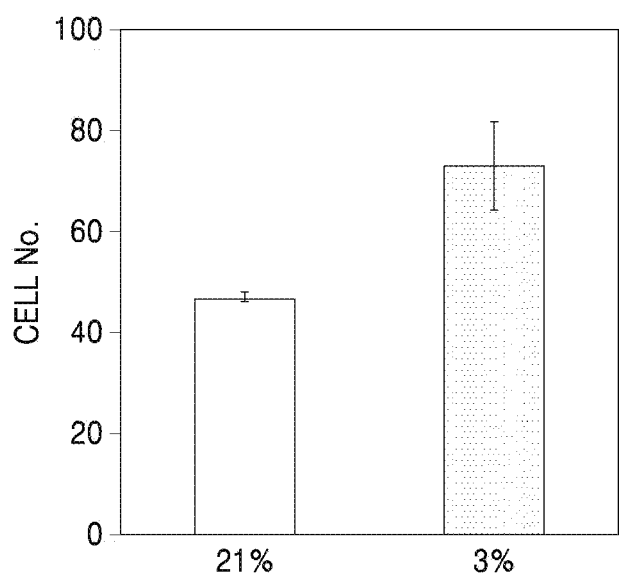

Further, to analyze cell's ability to migrate to damaged tissues, the upper surface of the transwell filter was coated with 0.1% gelatin at 37° C. for 1 hour. $5 \times 10^5$ cells were suspended in 100 µl of serum-free medium, and seeded to the upper chamber of the transwell insert. Before seeding, the cells were starved in the serum-free medium overnight. 600 µl of a medium (CS-CM) containing chemostats was added to the lower chamber. Cells were cultured in an incubator overnight. Cells remaining on the upper side of the filter were removed by using a cotton swab soaked with cold PBS. The transwell filter was cut by using a scalpel, followed by giemsa's staining. The bottom side was up and put on a slide glass and mounted. The migrating cells were examined by counting the number of stained cells under an optical microscope. The results are shown FIG. 2D.

FIG. 2 shows comparison between a hypoxia condition and a normoxia condition in the culturing of the enhanced umbilical cord-derived adherent stem cells according to a specific embodiment. As shown in FIGS. 2A and 2B, cells cultured under the hypoxia condition showed a rapid cell proliferation rate of a short doubling time. Further, as shown in FIG. 2C, the number of colonies was increased about twice, and as shown in FIG. 2D, cell's ability to migrate to damaged tissues was improved about 1.6 times.

2. Characterization of Enhanced Umbilical Cord-derived Adherent Stem Cells (2.1) Analysis of Genetic Stability of Enhanced Umbilical Cord-derived Adherent Stem Cells In order to analyze genetic stability of the enhanced umbilical cord-derived adherent stem cells prepared in (1.1) and (1.3), CTC-Banding analysis was performed.

In detail, DNAs were extracted from cells of P7 and P14 by using a Promega DNA extraction kit, and used as samples. An Illumina HumanOmni1-Quad Chip was used and iSCAN® scanner was used for measurement. First, 400 ng of each DNA sample was amplified by whole genome amplification, and randomly fragmented by a chemical method, and then purified by 2-propanol precipitation. The chip was pretreated with a buffer solution, and then the DNA sample was applied to the chip. After incubation for about 16 hours, staining, allele specific primer extension (ASPE), hybridization, target removal, and washing were performed. Thereafter, scanning was performed by IlluminaiScan, and data were analyzed by using a GenomeStudio® software. The results are shown in FIG. 3.

Figure 3:
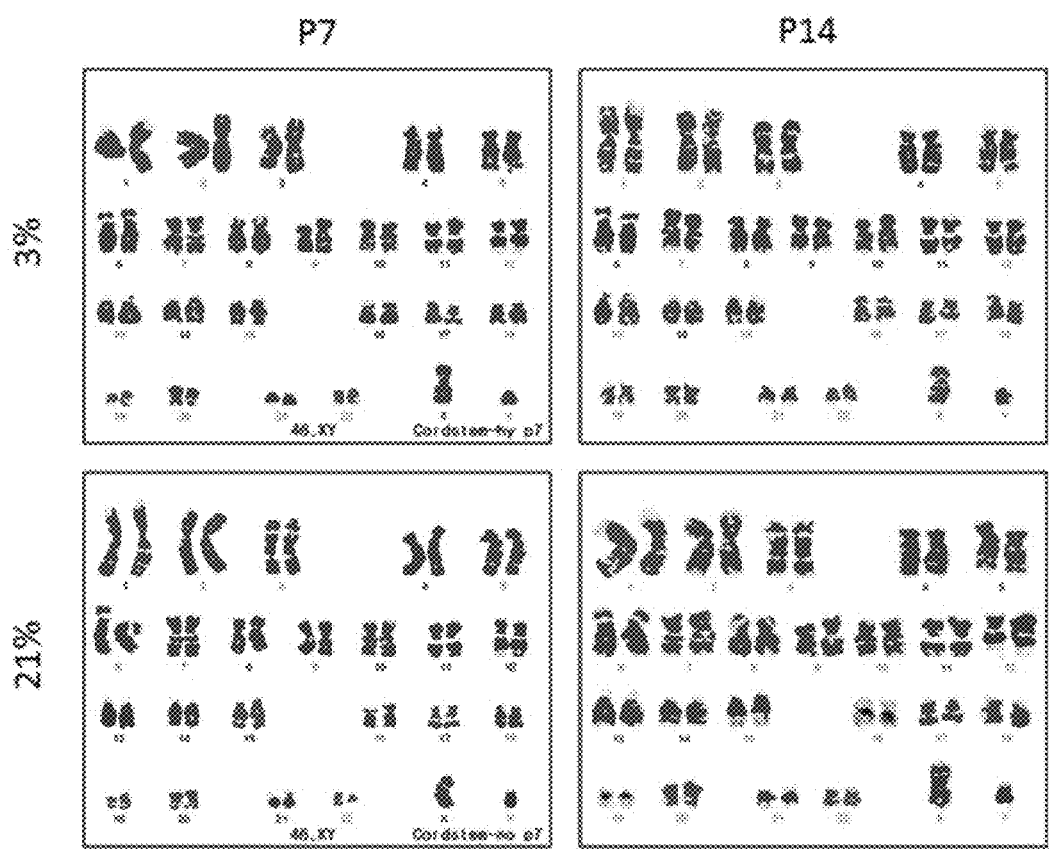
FIG. 3 shows results of karyotyping for examining genetic stability of the enhanced umbilical cord-derived adherent stem cells according to a specific embodiment.

FIG. 3 shows results of karyotyping for examining genetic stability of the enhanced umbilical cord-derived adherent stem cells according to a specific embodiment.

As shown in FIG. 3, the enhanced umbilical cord-derived adherent stem cells prepared by the preparation method according to a specific embodiment showed no genetic abnormalities until they were cultured to P14.

(2.2) Surface Protein Analysis of Enhanced Umbilical Cord-derived Adherent Stem Cells In order to analyze surface proteins of the enhanced umbilical cord-derived adherent stem cells prepared in (1.1), flow cytometry and immunofluorescence staining analysis were performed.

In detail, for flow cytometry, cells were washed with DPBS, and then reacted with Tra-1-60, CD3, CD1a, CD11 c, CD16, CD14, CD86, CD8a, CD19, CD40, CD80, CD200, CD141, CD61, CD87, MIC A/B, SSEA4 markers in 2% FBS-containing DPBS on ice for 20 minutes. Then, surface antigens were analyzed by FACS Calibur (Becton Bickinson), and the results are shown in FIG. 4A.

Figure 4A:
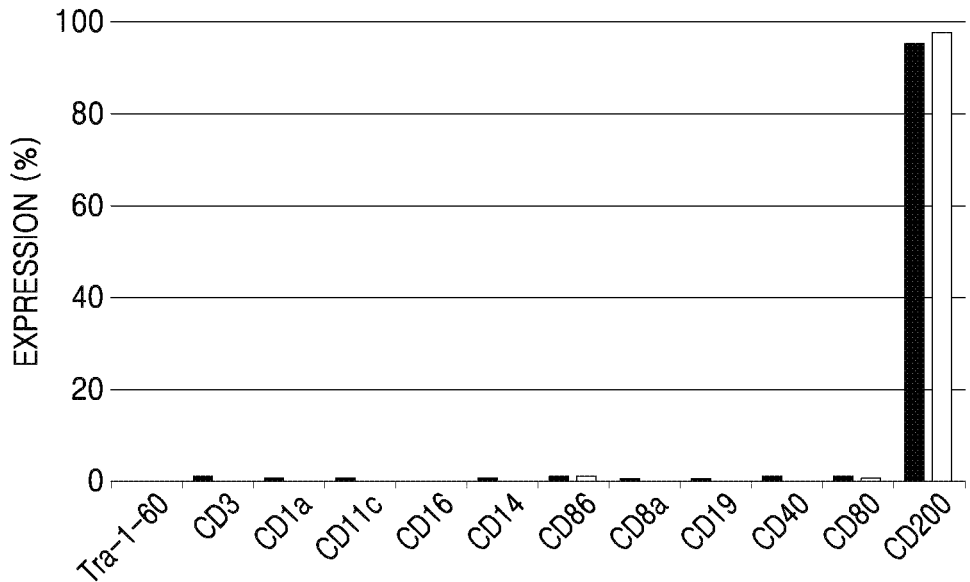
FIG. 4 shows results of analyzing surface proteins of the enhanced umbilical cord-derived adherent stem cells according to a specific embodiment.

To examine expression of Oct4 and Nanog which are embryonic stem cell markers, immunofluorescence staining was performed. First, cells were washed with DPBS three times, and then fixed with 4% paraformaldehyde in a culture plate at room temperature for 10 minutes. After fixation, cells were washed with DPBS three times. Next, the cells were permeated with 0.2% Triton X-100 solution at room temperature for 10 minutes, and washed with DPBS three times. Blocking was performed by using 10% normal goat serum at room temperature for 30 minutes. Primary antibodies (Oct4, Nanog) were added, and reacted overnight at 4° C. in the dark. Thereafter, the cells were washed with DPBS three times, and secondary antibodies were added thereto, and reacted at room temperature for 1 hour. Lastly, the cells washed with DPBS three times, and observed under a fluorescence microscope. The results are shown in FIG. 4B.

Figure 4A:
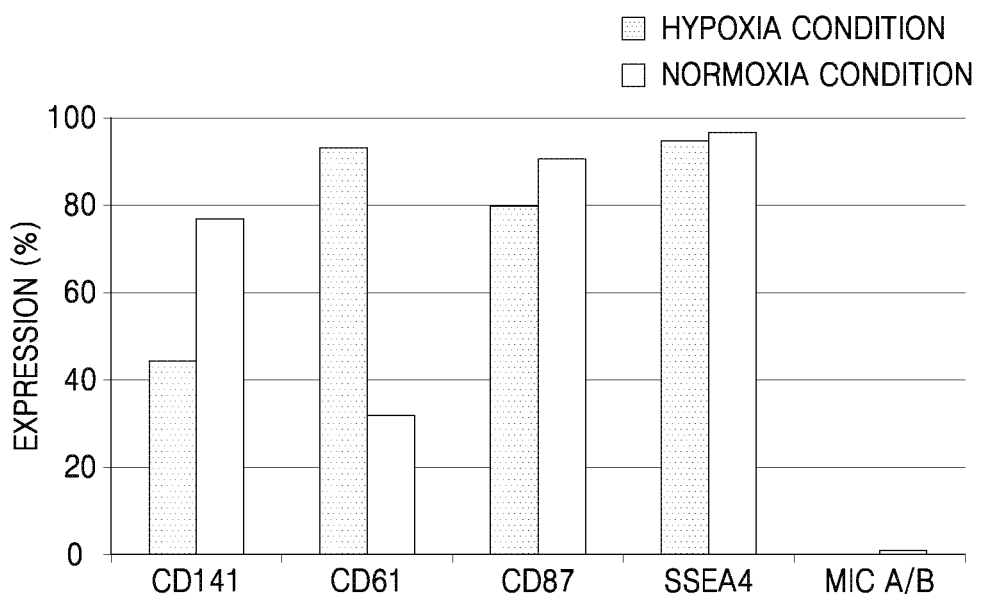
Figure 4B:
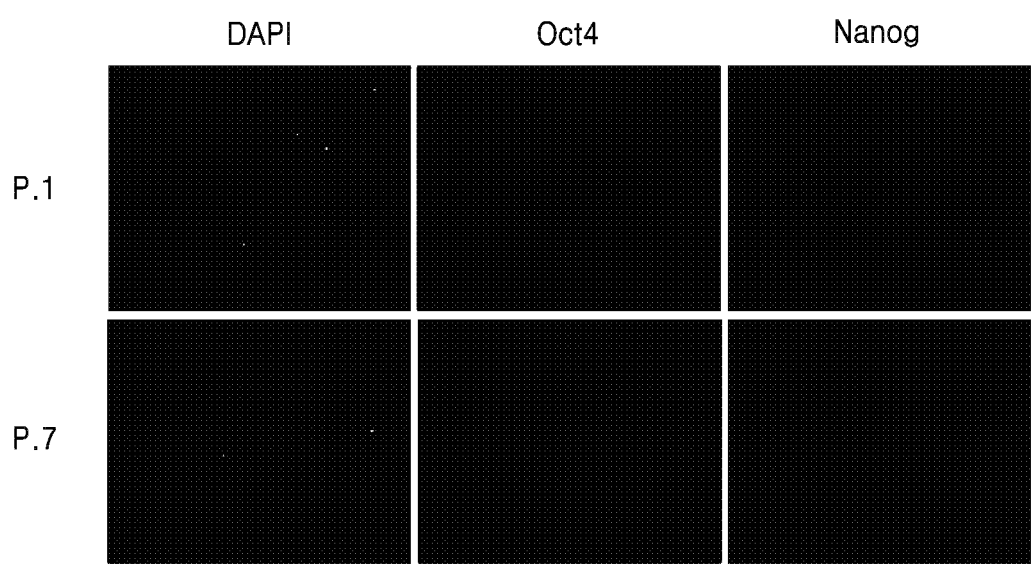

FIG. 4 shows results of analyzing surface proteins of the enhanced umbilical cord-derived adherent stem cells according to a specific embodiment.

As shown in FIG. 4A, the enhanced umbilical cord-derived adherent stem cells according to a specific embodiment were cells selectively positive for CD200, CD141, CD61, CD87 SSEA4, and selectively negative for TRA-1, CD3, CD1a, CD11 c, CD16, CD86, CD8a, CD40, MIC A/B, and additionally, selectively positive for CD61 under a hypoxia condition. Further, as shown in FIG. 4B, the enhanced umbilical cord-derived adherent stem cells according to a specific embodiment did not express Oct4 and Nanog proteins which are embryonic stem cell-specific markers.

(2.3) Analysis of Differentiation Ability of Enhanced Umbilical Cord-derived Adherent Stem Cells (2.3.1) Analysis of Adipocyte Differentiation Ability Analysis of adipocyte differentiation ability of the enhanced umbilical cord-derived adherent stem cells was performed as follows.

Figure 5:
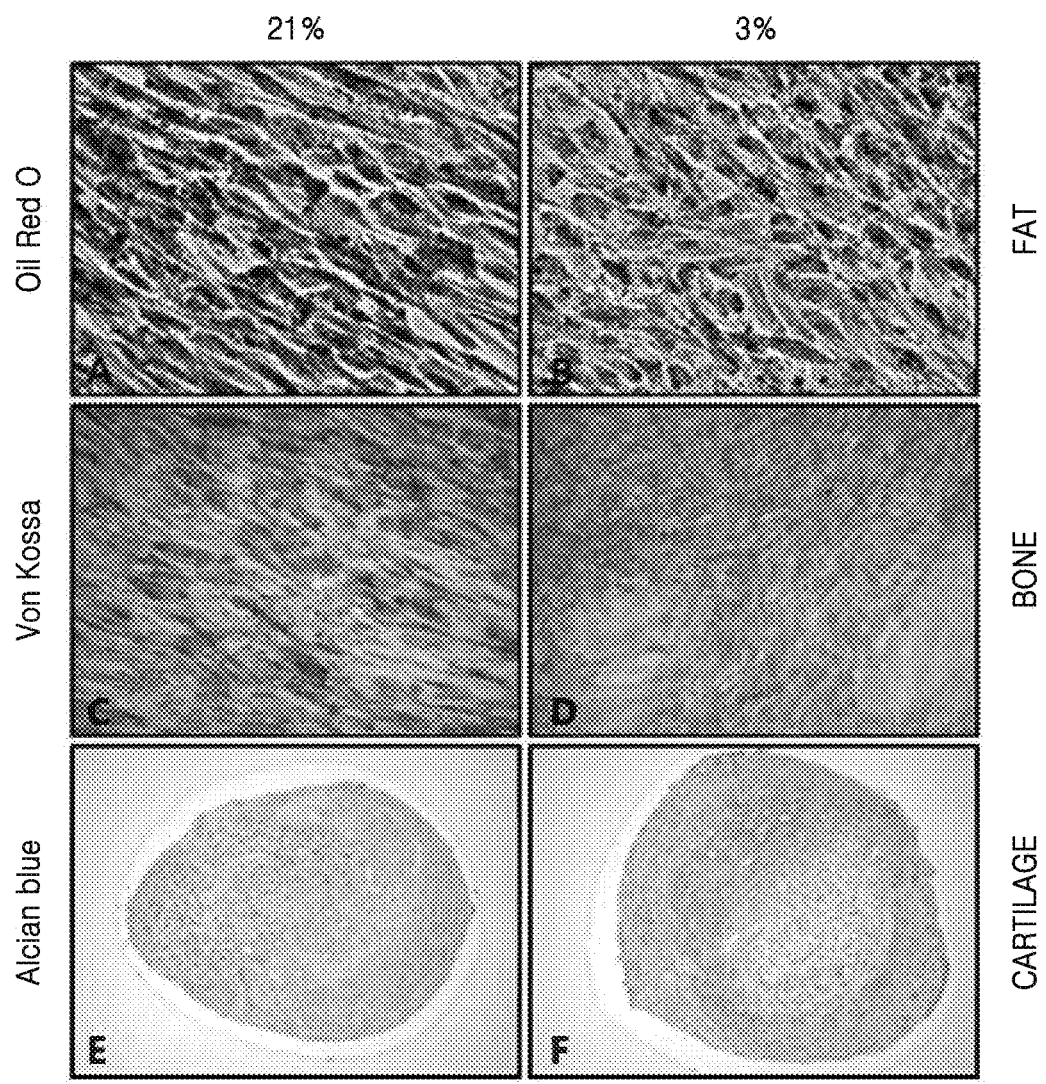
FIG. 5 shows results of analyzing multipotency of the enhanced umbilical cord-derived adherent stem cells according to a specific embodiment.

The enhanced umbilical cord-derived adherent stem cells prepared in (1.1) and (1.3) were cultured in an adipogenesis differentiation medium (StemPro® Adipogenesis Differentiation Kit, Life Technology) for 2 wee ks while replacing the medium every three days. Then, the culture medium was removed and cells were washed with Ca/Mg free DPBS, and reacted with 4% paraformaldehyde at room temperature for 15 minutes. The cells were washed with 60% isopropanol and then reacted with Oil Red O for 10 minutes. Then, the cells were washed with purified water, and adipocytes were observed under a microscope. The results are shown in FIG. 5.

(2.3.2) Analysis of Osteocyte Differentiation Ability

Analysis of osteocyte differentiation ability of the enhanced umbilical cord-derived adherent stem cells was performed as follows.

The enhanced umbilical cord-derived adherent stem cells prepared in (1.1) and (1.3) were cultured in an osteogenesis differentiation medium (StemPro® Osteogenesis Differentiation Kit, Life Technology) for 2 weeks while replacing the medium every three days. Then, the culture medium was removed and cells were washed with Ca/Mg free DPBS, and reacted with 4% paraformaldehyde at room temperature for 15 minutes. After reaction, the cells were washed with purified water, and reacted with a 1% silver nitrate solution at room temperature for 15 minutes. The cells were washed with purified water and then reacted with a 5% sodium thiosulfate solution at room temperature for 5 minutes. Then, the cells were washed with purified water, and reacted with a 0.1% nuclear fast red solution at room temperature for 5 minutes. Then, the cells were washed with purified water, and calcium deposition sample was observed under a microscope. The results are shown in FIG. 5.

(2.3.3) Analysis of Chondrocyte Differentiation Ability

Analysis of chondrocyte differentiation ability of the enhanced umbilical cord-derived adherent stem cells was performed as follows.

$2\times10^5$ of the enhanced umbilical cord-derived adherent stem cells prepared in (1.1) and (1.3) were put in a 15 ml tube, and centrifuged at 1,500 rpm for 5 minutes. The supernatant was discarded, and only cells were cultured in a chondrogenesis differentiation medium (StemPro® Chondrogenesis Differentiation Kit, Life Technology) with a lid closed loosely for 3 weeks while replacing the medium every three days. Then, the cell mass was made into a paraffin block and cut, followed by Alcian blue staining. Thereafter, chondrocytes stained with blue color were analyzed by optical microscope and the results are shown in FIG. 5.

FIG. 5 shows results of analyzing multipotency of the enhanced umbilical cord-derived adherent stem cells according to a specific embodiment.

As shown in FIG. 5, the result of analyzing adipocyte differentiation ability showed that large and small substances (fat), like droplets, were identified in red. Further, the result of analyzing osteocyte differentiation ability showed deposition of black brown calcium particles on the pink background. Further, the result of analyzing chondrocyte differentiation ability showed that during differentiation into chondrocytes, glycoproteins representing the rigidity and elasticity of cartilage were secreted and identified in blue. These results showed that the enhanced umbilical cord-derived adherent stem cells according to a specific embodiment prepared by the method of (1.1) and (1,3) may differentiate into adipocytes, osteocytes, or chondrocytes, indicating multipotency.

(2.4) Profiling and Quantification Analysis of Secretory Proteins of Enhanced Umbilical Cord-derived Adherent Stem Cells In order to analyze secretory proteins of the enhanced umbilical cord-derived adherent stem cells prepared in (1.1), multiplex bead analysis (MILLIPLEX Human Cytokine/Chemokine Panel 1, Merck Millipore, Billerica, Ma., USA) was performed.

In detail, the enhanced umbilical cord-derived adherent stem cells were cultured for 24 hours, and the culture thereof was incubated with antibody-coated capture beads at room temperature for 2 hours, followed by washing. The beads were incubated with biotin-labeled anti-human cytokine and chemokine antibody for 1 hour and incubated with streptavidin phycoerythrin for 30 minutes. Lastly, the beads were washed, and for quantification, a Luminex 200 program was used to analyze expression levels of secretory proteins. The results are shown in Table 2.

TABLE 2

| Category | Cytokine | (pg/ml) | 3% oxygen partial pressure |
|---|---|---|---|
| Inflammation | IFNr | | 46 |
| | IL-1a | | 19 |
| | IL-1b | | 5 |
| | IL-1ra | | 30 |
| | IL-2 | | 0 |
| | IL-3 | | 5 |
| | IL-4 | | 8 |
| | IL-5 | | 0 |
| | IL-6 | | 744 |
| | IL-7 | | 20 |
| | IL-8 | | >10,000 |
| | IL-9 | | 1 |
| | IL-10 | | 0 |
| | IL-12(p40) | | 14 |
| | IL-12(p70) | | 2 |
| | IL-13 | | 1 |
| | IL-15 | | 1 |
| | IL-17 | | 0 |
| | TNFa | | 0 |
| | TNFb | | 0 |
| | IFNa2 | | 50 |
| | MDC | | 2 |
| | sCD40L | | 0 |
| | sIL-2Ra | | 4 |
| Chemotaxis/Recruitment/Hematopoiesis | Eotaxin | | 117 |
| | Flt-3 Ligand | | 6 |
| | G-CSF | | 3,001 |
| | GM-CSF | | 46 |
| | MCP-1 | | >10,000 |
| | MCP-3 | | 1,033 |
| | MIP-1a | | 13 |
| | MIP-1b | | 2 |
| | RANTES | | 7 |
| | Fractalkine | | 116 |
| | IP-10 | | 10 |
| Angiogenesis/Tissue remodeling | VEGF | | 170 |
| Growth factor/fibrosis | EGF | | 16 |
| | GRO | | >10,000 |
| | PDGF-AA | | 0 |
| | PDGF-AB/BB | | 0 |
| | FGF-2 | | 90 |
| | TGFa | | 0 |
| Growth factor/fibrosis | IFG-1SR | | 197 |
| Growth factor/fibrosis | IGFBP3 | | 106.5 |
| Cell adhesion | epCAM | | 140.5 |

As shown in Table 2, it can be seen that the enhanced umbilical cord-derived adherent stem cells according to a specific embodiment secrete IL-6, IL-B, G-CSF, GM-CSF, MCP-1, MCP-3 VEGF, GRO, 1GF-1 SR, EpCAM, IGFBP3, etc.

(2.5) Analysis of Gene Expression of Enhanced Umbilical Cord-derived Adherent Stem Cells Gene expressions of the enhanced umbilical cord-derived adherent stem cells prepared in (1.1) were analyzed by comparing with those of bone marrow stem cells.

In detail, to analyze genes specifically expressed in enhanced umbilical cord-derived adherent stem cells by comparing with those of bone marrow stem cells, RNAs were extracted from the enhanced umbilical cord-derived adherent stem cells and bone marrow stem cells, followed by labelling and purification. Labeled cDNAs were hybridized with an illumina expression beadchip to obtain results. Data were statistically analyzed, and shown in the following Table 3 and FIG. 6.

TABLE 3

| ACCESSIOM | SYMBOL | Bone marrow stem cells/umbilical cord stem cells.fc | Bone marrow stem cells/umbilical cord stem cells.volume |
|---|---|---|---|
| NM_000088.3 | COL1A1 | −2.181493 | 15.1373 |
| NM_001552.2 | IGFBP4 | −2.824265 | 14.69699 |
| NM_003186.3 | TAGLN | −2.531752 | 14.55202 |
| NM_053056.2 | CCND1 | 3.063696 | 14.50615 |
| NM_000602.1 | SERPINE1 | 3.478237 | 14.50551 |
| NM_0010801 | PRNP | 2.289925 | 14.48807 |
| NM_002966.1 | S100A10 | −2.008462 | 14.47747 |
| NM_003900.3 | SQSTM1 | −2.009802 | 14.37823 |
| NM_005953 | MT2A | 2.116453 | 14.37452 |
| NM_001011546.1 | DSTN | −2.02492 | 14.31394 |
| NM_133505.2 | DCN | −6.032783 | 14.27855 |
| NM_006623.2 | PHGDH | −2.777842 | 14.05087 |
| NM_006486.2 | FBLN1 | −2.856691 | 14.04878 |
| NM_014220.2 | TM4SF1 | 2.298303 | 14.04031 |
| NM_003542.3 | HIST1H4C | 2.048184 | 14.0358 |
| NM_005928.1 | MFGE8 | −4.522915 | 14.01616 |
| NM_000269.2 | NME1 | 2.074511 | 14.00612 |
| NM_002116.5 | HLA-A | −2.348384 | 13.95215 |
| NM_138440.2 | VASN | −2.024294 | 13.87727 |
| NM_018689.1 | KIAA1199 | −3.846874 | 13.85275 |
| NM_003155.2 | STC1 | −76.224696 | 10.428439 |
| NM_001031692.1 | LRRC17 | −48.150192 | 9.539232 |
| NM_033439.2 | IL33 | −54.158215 | 8.92943 |
| NM_000104.2 | CYP1B1 | 349.556757 | 10.016027 |

Figure 6:
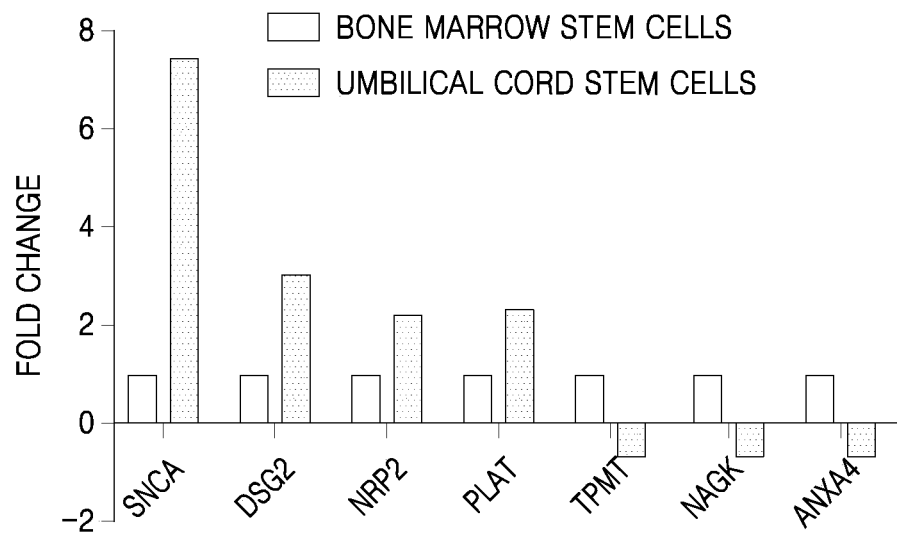
FIG. 6 shows results of comparing and analyzing protein expressions of the enhanced umbilical cord-derived adherent stem cells according to a specific embodiment.
Figure 6:
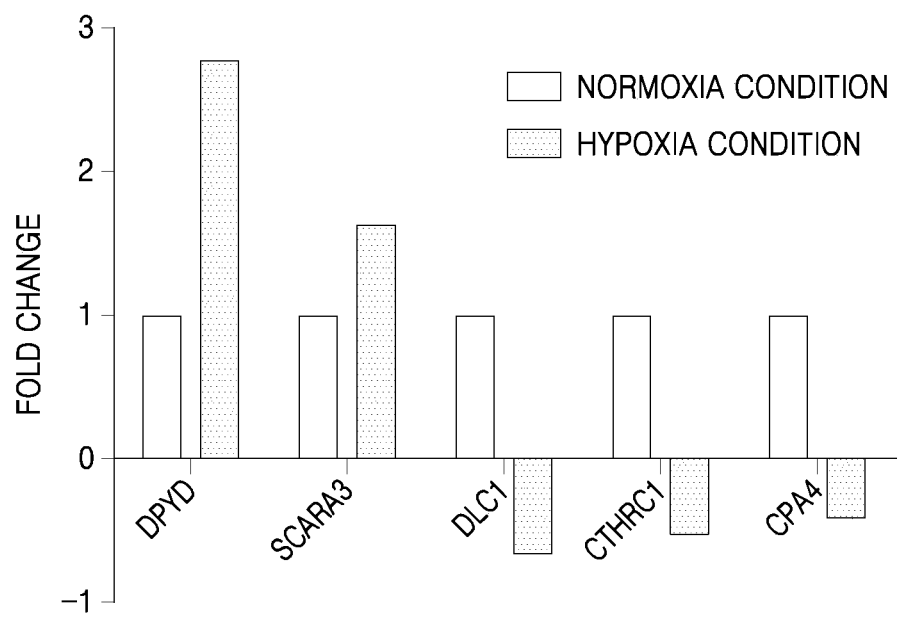

As shown in Table 3 and FIG. 6, high expression of COL1A1, IGFBP4, TAGLN, S100A10, SQSTM1, DSTN, DCN, PHGDH, FBLN1, MFGE8, HLA-A, VASN, KIAA1199, STC1, LRRC17, IL33, SNCA, DSG2, NRP2, PLAT was observed in the enhanced umbilical cord-derived adherent stem cells and low expression of CCND1, SERPINE1, PRNP, MT2A, TM4SF1, HIST1H4C, NME1, CXCL6, NTSR1, PTGS2, CYP1B1, TPMT, NAGK, ANXA4 was observed in the enhanced umbilical cord-derived adherent stem cells, as compared with bone marrow stem cells.

Among the genes, COL1A1 which is a highly expressed gene is alpha-1 type I collagen, and known to be expressed in collagen of connective tissues including cartilage. However, there are no reports about association between this gene and the enhanced umbilical cord-derived adherent stem cells.

Among the genes, IGFBP4 which is a highly expressed gene is an, insulin-like growth factor-binding protein, and known as a protein inhibiting various cancer cells. There is a report that IGFBP4 is detected in the serum of the cord blood, but there are no reports about association between this gene and the enhanced umbilical cord-derived adherent stem cells.

Among the genes, TAGLN which is a highly expressed gene is a gene expressed in fibroblast and smooth muscle, and its function has not been revealed yet. There is a report that TAGLN is expressed in bone marrow stem cells, but there are no reports about association between this gene and the enhanced umbilical cord-derived adherent stem cells.

Among the genes, CCND1 which is a poorly expressed gene is Cyclin D1. Overexpression of CCND1 leads to rapid transition from G1-phase to S-phase of the cell cycle to facilitate cell growth. There are reports that CCND1 is highly expressed in cancer cells, and umbilical cord blood stem cells inhibit 06 glioma via downregulation of CCND1. However, there are no reports about association between this gene and the enhanced umbilical cord-derived adherent stem cells.

Among the genes, SERPINE1 which is a poorly expressed gene is known as an endothelial plasminogen activator inhibitor, and known to function as a tissue plasminogen activator (tPA). However, there are no reports about association between this gene and the enhanced umbilical cord-derived adherent stem cells.

Among the genes, PRNP which is a poorly expressed gene is a major prion protein (CD230), and known to be expressed in various tissues as well as in the nerve system. Abnormality of PRNP gene is reported to cause neurological disorder. However, there are no reports about association between this gene and the enhanced umbilical cord-derived adherent stem cells.

Gene expression of the enhanced umbilical cord-derived adherent stem cells prepared in (1.1) and (1.3) was compared and analyzed in the same manner as above, and the results are shown in the following Table 4 and FIG. 6.

TABLE 4

| ACCESSIOM | SYMBOL | HYPOXIA CONDITION/ NORMOXIA CONDITION. FC | HYPOXIA CONDITION/ NORMOXIA CONDITION. volume |
|---|---|---|---|
| NM_002966.1 | S100A10 | 2.012102 | 14.47873 |
| NM_000584.2 | IL8 | -2.15463 | 14.32136 |
| NM_000689.3 | ALDH1A1 | -2.96734 | 14.21048 |
| NM_004052.2 | BNIP3 | 2.986779 | 14.13839 |
| NM_000599.2 | IGFBP5 | 2.352086 | 13.89253 |
| NM_000291.2 | PGK1 | 2.558604 | 13.8367 |
| NM_000365.4 | TPI1 | 2.104472 | 13.77506 |
| AV762101 | | -2.06723 | 13.663111 |
| NM_133505.2 | DCN | 2.293184 | 13.6264 |
| NM_002633.2 | PGM1 | 2.334847 | 13.19009 |
| NM_000903.2 | NQO1 | -3.74919 | 13.18508 |
| NM_004566.2 | PFKFB3 | 2.690257 | 13.05599 |
| XM_927868.1 | LOC644774 | 3.03134 | 13.01144 |
| NM_000902.3 | MME | 2.705127 | 12.94125 |
| NR_031742.1 | MIR1978 | 2.384465 | 12.90422 |
| NM_000291.2 | PGK1 | 2.676001 | 12.843307 |
| NM_006931.1 | SLC2A3 | 2.061179 | 12.82325 |
| NM_003670.1 | BHLHB2 | 2.329298 | 12.81616 |
| NM_004331.2 | BNIP3L | 2.235896 | 12.7381 |
| NM_000599.2 | IGFBP5 | 3.068411 | 12.56565 |
| NM_020142.3 | NDUFA4L2 | 10.462756 | 8.883854 |

As shown in Table 4 and FIG. 6, high expression of S100A10, BNIP3, IGFBP5, PGK1, TPI1, DCN, PGM1, PFKFB3, LOC644774, MME, MIR1978, PGK1, SLC2A3, BHLHB2, BNIP3L, IGFBP5, NDUFA4L2, DPYD, and SCARA3 was observed in the enhanced umbilical cord-derived adherent stem cells cultured under a hypoxia condition and low expression of IL8, ALDH1A1, NQO1, DLC1, CTHRC1, and CPA4 was observed in the enhanced umbilical cord-derived adherent stem cells cultured under a hypoxia condition, as compared with those under a normoxia rendition.

Among the genes, S100A10 which is a highly expressed gene is S100 calcium-binding protein A10, and regulates cell cycle and differentiation. Further, S100A10 is known to function in exocytosis and endocytosis. S100A10 was studied as one of proteins highly expressed during differentiation of bone marrow stem cells into bone. However, there are no reports about association between this gene and the enhanced umbilical cord-derived adherent stem cells.

Among the genes, BNIP3 which is a highly, expressed gene is known to be highly expressed in DCB-MSC, when gene expression was compared at mRNA levels of UCB-MSC (umbilical cord blood-derived stem cells) and UCB-MNC (umbilical cord blood-derived blood cells). Further, amniotic stem cells were collected under a hypoxia condition, and then subjected to mRNA microassay analysis. As a result, BNIP3 gene is known to be significantly increased under the hypoxia condition. However, there are no reports about association between this gene and the enhanced umbilical cord-derived adherent stern cells.

Among the genes, IGFBP5 which is a highly expressed gene is an insulin-like growth factor binding protein 5, and functions in development and locates in the extracellular space. Expression of IGFBP5 gene in bone marrow stem cells was reported, but there are no reports about association between this gene and the enhanced umbilical cord-derived adherent stem cells.

Among the genes, IL8 which is a poorly expressed gene is reported to be released from phagocytes and mesenchymal cells to activate neutrophils inducing chemotaxis when exposed to inflammatory environments. However, there are no reports about association between this gene and the enhanced umbilical cord-derived adherent stem cells.

Among the genes, ALDH1A1 which is a poorly expressed gene is aldehyde dehydrogenase family 1, member A1, and is an enzyme involved in the major oxidation pathway of alcohol metabolism. However, there are no reports about association between this gene and the enhanced umbilical cord-derived adherent stem cells.

3. Analysis of Anti-inflammatory, Vascular Regeneration, and Nerve Regeneration Effects of Enhanced Umbilical Cord-derived Adherent Stem cells (3.1) Analysis of Anti-inflammatory Effect of Enhanced Umbilical Cord-derived Adherent Stem Cells To analyze an anti-inflammatory effect of the enhanced umbilical cord-derived adherent stem cells prepared in (1.1), PBMC proliferation-inhibiting ability and IL-10 secreted from activated PBMC were analyzed.

In detail, PBMC proliferation-inhibiting ability was analyzed as follows. First, the enhanced umbilical cord-derived adherent stem cells were inoculated at different concentrations in a 24-well plate and cultured for 24 hours. Thereafter, CFSE-stained PBMC was stimulated by addition of PHA, and co-cultured with the enhanced umbilical cord-derived adherent stem cells for 5 days. Thereafter, whether inflammation was inhibited by cytokines secreted by the enhanced umbilical cord-derived adherent stem cells or inhibited by direct cell-to-cell contact was examined by presence or absence of transwell. The results are shown in FIG. 7A.

Further, to analyze IL-10 secreted from activated PBMC, the co-culture was performed for 5 hours and for 5 days, and then the conditioned medium was collected. The amount of secreted IL-10 was measured by using human IL-10 ELISA kit (R&D Systems), and the results are shown in FIG. 7A.

Figure 7A:
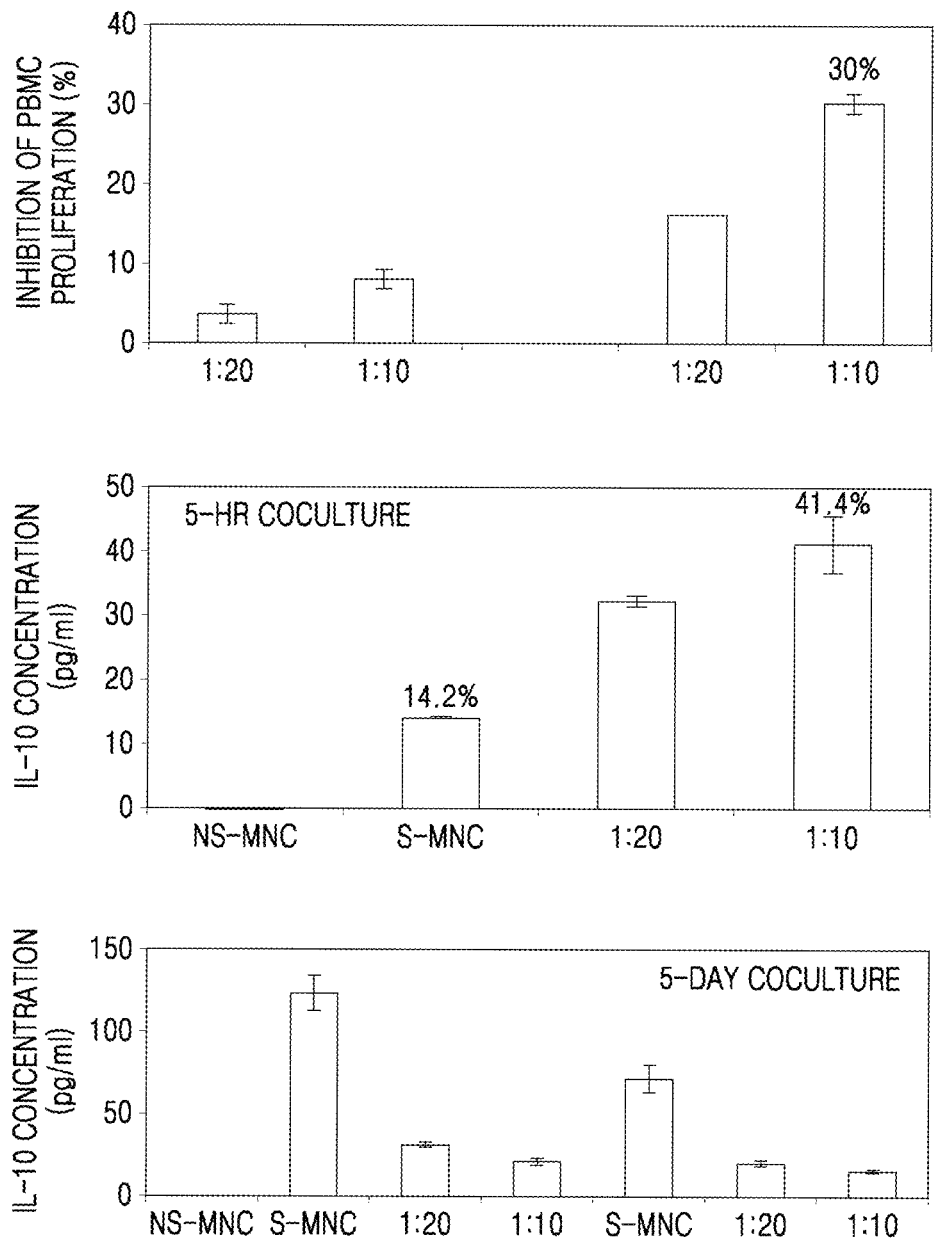
FIG. 7A shows results of analyzing an anti-inflammatory effect of the enhanced umbilical cord-derived adherent stem cells according to a specific embodiment.

FIG. 7A shows results of analyzing the anti-inflammatory effect of the enhanced umbilical cord-derived adherent stem cells according to a specific embodiment.

As shown in FIG. 7A, the enhanced umbilical cord-derived adherent stem cells according to a specific embodiment inhibited PBMC proliferation, as compared with a control group. Further, when a ratio of enhanced umbilical cord-derived adherent stem cells: PBMC is 1:10, up to about 30.51±1.74% of PBMC proliferation inhibition was observed by indirect co-culture. Further, the results of analyzing IL-10 secreted from activated PBMC showed that activated PBMC secreted anti-inflammatory cytokine (IL-10), and the enhanced umbilical cord-derived adherent stem cells function to increase IL-10 secretion of PBMC The results suggest that the enhanced umbilical cord-derived adherent stem cells according to a specific embodiment may be usefully applied to treatment of inflammatory diseases.

(3.2) Analysis of Vascular Regeneration Effect of Enhanced Umbilical Cord-derived Adherent Stem Cells To analyze a vascular regeneration effect of the enhanced umbilical cord-derived adherent stem cells prepared in (1.1), vascular endothelial cell proliferation was analyzed.

In detail, EBM-2 and conditioned medium of the enhanced umbilical cord-derived adherent stem cells were collected and prepared as samples. Thereafter, vascular endothelial cells (HUVECs) were inoculated in a 96-well plate. When the cells were proliferated for about 1 day, EBM-2 and the culture medium of the enhanced umbilical cord-derived adherent stem cells were added thereto, respectively and cultured for 4 days. A reagent of Cyto X™ Cell viability assay kit (WST-1) was added to the medium at an amount of 10% thereof, and allowed to react in an incubator for 2 hours to 3 hours. Thereafter, vascular endothelial cell proliferation rates were analyzed at 450 nm by using a microreader, and the results are shown in FIG. 7B.

FIG. 7B shows results of analyzing the vascular regeneration effect of the enhanced umbilical cord-derived adherent stem cells according to a specific embodiment.

As shown in FIG. 7B, when the proliferation rate of the vascular endothelial cells cultured in EBM-2 medium was taken as 100%, the proliferation rate of the vascular endothelial cells cultured in the conditioned medium of the enhanced umbilical cord-derived adherent stem cells was 172±15.22%.

The result suggests that the enhanced umbilical cord-derived adherent stem cells according to a specific embodiment have the vascular regeneration effect.

(3.3) Analysis of Nerve Regeneration Effect of Enhanced Umbilical Cord-derived Adherent Stem Cells To analyze a nerve regeneration effect of the enhanced umbilical cord-derived adherent stem cells prepared in (1.1), nerve cell proliferation was analyzed.

In detail, MEM and conditioned medium of the enhanced umbilical cord-derived adherent stem cells were collected and prepared as samples. Thereafter, nerve cells (SH-SY5Y) were inoculated in a 96-well plate. When the cells were proliferated for about 1 day, MEM and the culture medium of the enhanced umbilical cord-derived adherent stem cells were added thereto, respectively and cultured for 4 days. A reagent of Cyto X™ Cell viability assay kit (WST-1) was added to the medium at an amount of 10% thereof, and allowed to react in an incubator for 2 hours to 3 hours. Thereafter, nerve cell proliferation rates were analyzed at 450 nm by using a microreader, and the results are shown in FIG. 7C.

FIG. 7C shows results of analyzing the nerve regeneration effect of the enhanced umbilical cord-derived adherent stem cells according to a specific embodiment.

As shown in FIG. 7C, when the proliferation rate of the nerve cells cultured in MEM medium was taken as 100%, the proliferation rate of the nerve cells cultured in the conditioned medium of the enhanced umbilical cord-derived adherent stem cells was 302±15.97%.

The result suggests that the enhanced umbilical cord-derived adherent stem cells according to a specific embodiment have the nerve regeneration effect.

The invention claimed is:

1. A composition comprising enhanced adherent stem cells that are isolated from a single source and cultured under a hypoxia condition and a pharmaceutically acceptable carrier,
   wherein the single source is a mammalian umbilical cord, and
   wherein the enhanced adherent stem cells have the following characteristics (a) to (f):
   (a) having a high expression level of TAGLN, and having a high expression of one or more selected from the group consisting of STC1, LRRC17, and IL33, as compared with bone marrow stem cells;
   (b) having a low expression level of ANXA4, TPMT, and NAKG, and having a low expression level of one or more selected from the group consisting of CCND1, SERPINE1, and PRNP, as compared with bone marrow stem cells;
   (c) maintaining the morphology of adherent fibroblasts during subculture;
   (d) having ability to differentiate into adipocytes, osteocytes, and chondrocytes;
   (e) having one or more surface antigen characteristics selected from the group consisting of CD200+, Tra1-60−, CD3−, CD1a−, CD11c−, CD16−, CD86a−, CD8a−, CD40−, CD141+, CD61+, CD87+, and MIC A/B−; and
   (f) having surface antigen characteristics of Oct4− and Nanog−.

2. The composition of claim 1, wherein the enhanced adherent stem cells further have one or more characteristics selected from the following (g) to (j):
   (g) having a high expression level of one or more selected from the group consisting of S100A10, BNIP3, IGFBP5, NDUFA4L2, DPYD, and SCARA3, as compared with those cultured under a normoxia condition;
   (h) having a low expression level of one or more selected from the group consisting of IL8, ALDH1A1, DLC1, CTHRC1, and CPA4, as compared with those cultured under a normoxia condition;
   (i) having a high expression level of one or more selected from the group consisting of SNCA, DSG2, NRP2, and PLAT, as compared with bone marrow stem cells; and
   (j) having a low expression level of one or more selected from the group consisting of TPMT, NAGK, and ANXA4, as compared with bone marrow stem cells.

3. The composition of claim 1, wherein the characteristics of (a) and (b) show that the expression level difference from that of the bone marrow stem cells is twice or more, as measured by microarray.

4. The composition of claim 2, wherein the characteristics of (g) and (h) under hypoxia condition show that the expression level difference from those under the normoxia condition is twice or more, as measured by microarray analysis or proteomic analysis.

5. The composition of claim 1, wherein the enhanced adherent stem cells have colony-forming ability.

6. The composition of claim 1, wherein the enhanced adherent stem cells secrete IL-6, IL-8, G-CSF, GM-CSF, MCP-3, VEGF, GRO, IFNγ, IL-1a, IL-1b, IL-1ra, IL-3, IL-4, IL-7, IL-9, IL-12(p40), IL-13, IL-14, IFNα2, MDC, sIL-2Ra, Eotaxin, Flt-3 ligand, MCP-1, MIP-1a, MIP-1b, RANTE, fractalkine, IP-10, EGF, FGF-2, IGF-1 SR, EpCAM, IGFBP3, or a combination thereof.

7. The composition of claim 1, wherein the enhanced adherent stem cells are derived from the Wharton's Jelly tissue of a mammalian umbilical cord.

8. A method of preparing the composition according to claim 1, the method comprising:
- adherent-culturing isolated umbilical tissue pieces on a culture plate until cells extend from the cultured tissue;
- isolating enhanced umbilical cord-derived adherent stem cells by contacting the cultured umbilical cord with a dissociation enzyme, and
- subculturing the isolated enhanced umbilical cord-derived adherent stem cells under a hypoxia condition.

9. The method of claim 8, wherein the subculturing further comprises treating animal component-free (ACF) recombinant enzyme before cell transplantation for subculturing.

10. The method of claim 8, wherein the subculturing is performed in a medium containing fibroblast growth factor 4 (FGF-4) and heparin.

11. The method of claim 8, wherein the subculturing is performed from 3 to 15 passages.

12. The method of claim 8, wherein the dissociation enzyme is collagenase.

\* \* \* \* \*